(12) United States Patent
Lennox

(10) Patent No.: US 7,241,307 B2
(45) Date of Patent: Jul. 10, 2007

(54) METHOD AND APPARATUS FOR MANAGING TEMPERATURE IN A PATIENT

(75) Inventor: Charles D. Lennox, Hudson, NH (US)

(73) Assignee: MedCool, Inc., Westwood, MA (US)

( * ) Notice: Subject to any disclaimer, the term of this patent is extended or adjusted under 35 U.S.C. 154(b) by 469 days.

(21) Appl. No.: 10/758,687

(22) Filed: Jan. 15, 2004

(65) Prior Publication Data

US 2005/0027281 A1    Feb. 3, 2005

Related U.S. Application Data

(63) Continuation-in-part of application No. 10/330,638, filed on Dec. 27, 2002, now Pat. No. 7,156,867.

(60) Provisional application No. 60/440,279, filed on Jan. 15, 2003, provisional application No. 60/344,986, filed on Dec. 31, 2001.

(51) Int. Cl.
*A61F 7/12* (2006.01)
(52) U.S. Cl. .................................. 607/104; 607/105
(58) Field of Classification Search ............ 604/113, 604/508; 607/96, 104, 106
See application file for complete search history.

(56) References Cited

U.S. PATENT DOCUMENTS

| | | | |
|---|---|---|---|
| 3,064,649 A | 11/1962 | Fuson | 128/214 |
| 3,640,340 A | 2/1972 | Leonard et al. | 165/166 |
| 3,982,535 A | 9/1976 | Bahrton | 128/214 E |
| 3,998,222 A | 12/1976 | Shihata | 128/214 R |
| 4,075,091 A | 2/1978 | Bellhouse | 210/19 |
| 4,181,132 A | 1/1980 | Parks | 128/399 |
| 4,298,006 A | 11/1981 | Parks | 128/399 |
| 4,747,826 A | 5/1988 | Sassano | 604/52 |
| 4,894,164 A | 1/1990 | Polaschegg | 210/646 |
| 4,904,237 A | 2/1990 | Janese | 604/28 |

(Continued)

OTHER PUBLICATIONS

W. Behringer, et al., "Veno-Venous Extracorporeal Blood Shunt Cooling To Induce Mile Hypothermia In Dog Experiments And Review Of Cooling Methods", Resuscitation 54 (2002), p. 89-97.

(Continued)

*Primary Examiner*—Roy D. Gibson
(74) *Attorney, Agent, or Firm*—Thomas J. Engellenner; Charlton Shen; Nutter McClennen & Fish LLP

(57) ABSTRACT

A fluid transfer assembly includes a fluid carrier and a heat exchange assembly coupled to the fluid carrier. The heat exchange assembly includes a heat exchange conduit, a heat exchanger in thermal communication with the heat exchange conduit, and a pump. The pump defines a stroke volume that is greater than a fluid carrier volume defined by the fluid carrier. The configuration of the stroke volume of the pump and the fluid carrier volume of the fluid carrier limits the length of the fluid carrier. In such a configuration, the heat exchange assembly orients in proximity to the body during operation to create a relatively short ex vivo flow path between a body and the heat exchange assembly. During operation, as the fluid flows along the ex vivo flow path, the relatively short ex vivo flow path minimizes thermal change in the fluid caused by a heat exchange between the walls of the fluid carrier and the atmosphere.

47 Claims, 15 Drawing Sheets

U.S. PATENT DOCUMENTS

| | | | | |
|---|---|---|---|---|
| 4,908,014 A | * | 3/1990 | Kroyer | 604/6.13 |
| 5,074,838 A | * | 12/1991 | Kr.phi.yer | 604/6.13 |
| 5,342,301 A | | 8/1994 | Saab | 604/96 |
| 5,383,854 A | | 1/1995 | Safar et al. | 604/98 |
| 5,486,208 A | | 1/1996 | Ginsburg | 607/106 |
| 5,624,392 A | | 4/1997 | Saab | 604/43 |
| 5,662,127 A | | 9/1997 | De Vaughn | 128/765 |
| 5,843,112 A | | 12/1998 | De Vaughn | 606/181 |
| 5,968,009 A | | 10/1999 | Siman | 604/43 |
| 5,971,979 A | | 10/1999 | Joye et al. | 606/21 |
| 6,007,774 A | | 12/1999 | Faithfull et al. | |
| 6,106,497 A | | 8/2000 | Wang | 604/122 |
| 6,149,670 A | | 11/2000 | Worthen et al. | 607/3 |
| 6,156,007 A | | 12/2000 | Ash | 604/113 |
| 6,217,552 B1 | | 4/2001 | Barbut et al. | 604/113 |
| 6,217,582 B1 | | 4/2001 | Slocum | 606/87 |
| 6,368,304 B1 | | 4/2002 | Aliberto et al. | 604/113 |
| 6,379,378 B1 | | 4/2002 | Werneth et al. | 607/105 |
| 6,432,124 B1 | | 8/2002 | Worthen et al. | 607/105 |
| 6,458,150 B1 | | 10/2002 | Evans et al. | 607/105 |
| 6,460,544 B1 | | 10/2002 | Worthen | 128/898 |
| 6,579,496 B1 | * | 6/2003 | Fausset et al. | 422/44 |
| 6,623,514 B1 | | 9/2003 | Chin | 607/105 |
| 6,626,857 B1 | | 9/2003 | Ohta et al. | 604/6.13 |
| 6,648,878 B2 | | 11/2003 | Lafontaine | 606/21 |
| 6,648,906 B2 | | 11/2003 | Lasheras et al. | |
| 6,660,026 B2 | | 12/2003 | Larnard et al. | 607/104 |
| 6,682,508 B1 | | 1/2004 | Meythaler et al. | 604/246 |
| 6,682,551 B1 | | 1/2004 | Worthen et al. | 607/105 |
| 6,692,519 B1 | | 2/2004 | Hayes, Jr. | 607/105 |
| 6,699,269 B2 | | 3/2004 | Khanna | 607/105 |
| 6,726,710 B2 | | 4/2004 | Worthen et al. | 607/105 |
| 6,736,790 B2 | | 5/2004 | Barbut et al. | 604/6.13 |
| 2002/0085952 A1 | | 7/2002 | Ellingboe et al. | 422/45 |
| 2002/0198579 A1 | | 12/2002 | Khanna | 607/105 |
| 2003/0135152 A1 | | 7/2003 | Kollar et al. | 604/35 |

OTHER PUBLICATIONS

Piepgras, et al., "Rapid Active Internal Core Cooling for Induction of Moderate Hypothermia in Head Injury by Use of an Extracorporeal Heat Exchanger", Neurosurgery Online, Feb. 1998, vol. 42, No. 2. http://www.neurosurgery-online.com. Visited Nov. 24, 2003.

Alsius, A New Degree of Care, The Fortius Catheter, http://www.alsius.com/us/fortius.htm. Visited Nov. 24, 2003.

Hachimi-Idrissi, et al., "Mild Hypothermia Induced by a Helmut Device: A Clinical Feasibility Study", Resuscitation 51:275 (2001).

Ommaya, et al., "Direct Extravascular Brain Cooling in the Normothermic Animal", Neurology 12:882 (1962).

Tooley, et al., "Significant Selective Head Cooling can be Maintained Long-Term After Global Hypoxia Ischemia in Newborn Piglets", Pediatrics, vol. 109, No. 4, pp. 643-649, Apr. 2002.

Javid, et al., "Hypothermic Ventricular Perfusion: Evaluation of Use in Cerebrovascular Occlusion, New York State Journal of Medicine", pp. 248-251. Jan. 5, 1967.

Tooley, et al., "Head Cooling with Mild Systemic Hypothermia in Anesthetized Piglets is Neuroprotective", Annals of Neurology, vol. 53, No. 1, pp. 65-72, Jan. 2002.

White, M.D., "Cerebral Hypothermia and Circulatory Arrest: Review an Commentary", Mayo Clin. Proc. 53:450 (1978).

Costal, et al., "Experimental Production of Cerebral Hypothermia by Ventricular Perfusion Techniques", J. Neurosurg, 20:112 (1963).

* cited by examiner

METHOD AND APPARATUS FOR MANAGING TEMPERATURE IN A PATIENT

RELATED APPLICATIONS

This application is a continuation-in-part of U.S. Utility application Ser. No. 10/330,638, filed Dec. 27, 2002, now U.S. Pat. No. 7,156,867 the entire teachings of which are incorporated herein by reference, which claims benefit of U.S. Provisional Application 60/344,986 filed Dec. 31, 2001, the entire teachings of which are incorporated herein by reference. This application also claims benefit of U.S. Provisional Application Ser. No. 60/440,279, filed Jan. 15, 2003, the entire teachings of which are incorporated herein by reference.

BACKGROUND

Patients suffering from certain body injuries typically experience either an increase or decrease in body temperature as a result of the injury. For example, certain patients experience hyperthermia or fever following significant brain injury or major cardiovascular surgery. In another example, certain patients experience spontaneous hypothermia following cardiac arrest, brain trauma, or extensive bleeding. In both examples, the presence of a hypothermic or hypothermic state is prognostic of a poor neurological outcome or mortality of the patients and the patients typically require body temperature management to reverse the hyperthermic or hypothermic states. For example, in the case of a patient experiencing a hyperthermic state, healthcare professionals typically minimize or prevent fever in the patient using analgesic therapy and body surface cooling to reduce the patient's body temperature, improve neurological outcomes, and improve the likelihood of the patient's survival. In the case of a patient experiencing a hypothermic state, healthcare professionals typically increase the body temperature of the patient using body surface warming devices, such as heating blankets, to improve the likelihood of the patient's survival.

While heath care professionals utilize body temperature management to reverse the hyperthermic or hypothermic state of a patient, healthcare professionals also utilize body temperature management techniques to induce hypothermia in certain case. For example, the therapeutic use of mild to moderate hypothermia (temperature 2 to 5 degrees centigrade below normal) has been shown to reduce the secondary loss of vital organ tissue following an ischemic event such as stroke or cardiac arrest (e.g., heart attack), and following trauma. Therapeutic hypothermia also effectively reduces inflammation and edema in tissue following injury.

Historically, health care professionals have induced systemic hypothermia (e.g., whole body cooling) in a patient by immersing the patient's body in a cool bath. Currently, there are several conventional systemic hypothermia systems available. Such conventional systems include blankets or pads where cooled water is circulated through channels in the walls of the blanket or pad. As the patient's body contacts the walls of the blanket, the cooled water within the channels carries heat away from the patient's body, thereby inducing systemic hypothermia in the patient.

Health care professionals also use devices that provide vascular cooling to a patient to reduce the patient's body temperature. Such devices provide either in vivo and ex vivo cooling of blood, relative to the patient.

For example, a typical in vivo vascular cooling catheter, such as available from Radiant Medical Corporation, Alsius Medical, or InnerCool Medical, has a distal end placed within a vena cava of a patient and a proximal end coupled to refrigeration-based cooling console located in the vicinity of the patient (e.g., bedside). During operation, the console pumps cold saline through the catheter (e.g., from the console, to the distal end of the catheter, and back to the console). As blood flows through the vena cava, the blood contacts the distal end of the cooling catheter. The distal end of the cooling catheter acts as an in vivo heat exchanger, absorbing heat from the blood as the blood flows past the distal end of the catheter, while the cold saline within the catheter carries heat away from the blood, thereby cooling the blood and reducing the body temperature of the patient.

In another example, healthcare professionals typically utilize an ex vivo vascular cooling device during cardiovascular surgery. The use of hypothermia during cardiac surgery aids in protecting cardiac and cerebral tissues during periods of reduced blood circulation during the surgery. During cardiovascular surgery healthcare professionals perform a hypothermic bypass technique where blood is pumped from a patient, through a bedside machine that cools and oxygenates the blood, and back into the patient. The reduced temperature blood induces hypothermia within the patient

SUMMARY

Conventional techniques for obtaining an optimal therapeutic temperature in the body of a patient suffer from a variety of deficiencies.

As indicated above, health care workers typically use body surface cooling or body surface warming to either reduce or increase, respectively, the body temperature of the patient. For example, the induction of systemic hypothermia by external cooling modalities has been demonstrated to be effective in improving the outcomes from stroke, cardiac arrest, heart attack, trauma, and surgery. Induction of systemic hypothermia, however, can take several hours to lower a patient's body to therapeutic temperatures. The temperature and duration of therapeutic is limited by the ability of the patient to tolerate, or survive the therapy. Also, such a time period can create a delay in the patient achieving therapeutic temperatures and allows for the progression of irreversible secondary injury to vital tissues. Furthermore induction of systemic hypothermia in a patient typically results in side effects that typically include shivering, cardiac arrhythmia and arrest, pneumonia, infections, and coagulation disorders.

After a patient undergoes systemic hypothermia, at the end of the treatment, the healthcare worker exposes the patient to a rewarming period. During the "critical phase" or rewarming period of hypothermia treatment, the patient typically undergoes a sudden and critical increase in intracranial pressure. Currently, there is no effective way to manage a sudden and critical increase in intra-cranial pressure, since re-cooling the body to reverse the increase in intra-cranial pressure takes several hours.

Also as indicated above, health care professionals use in vivo devices that provide vascular cooling to a patient to reduce a patient's body temperature. In vivo devices, such as vascular cooling catheters, provide significantly faster cool down rates than external cooling modalities. Vascular cooling catheters, however, are expensive, highly invasive, require physicians with advanced intra-vascular procedure skills to place these catheters into the patient, and typically require the use of advanced imaging technologies. Vascular cooling catheters typically have also have a relatively large shaft diameter to accommodate a large flow of saline within the catheter (e.g., in two directions). Vascular cooling catheters also typically have a heat exchanger (e.g., the distal end of the catheter) configured with a relatively large surface area for exposure to a blood stream. Because of the large surface area exposed to blood, the resulting risk of surface clot formation and embolization minimizes or precludes the use of these types of catheters in the arterial vasculature. The relatively large size of the shaft diameter and the heat exchanger limits the use of these catheters to the vena cava. As such, the use of vascular cooling catheters limit the ability of a user to selectively alter the temperature of a specific area of the patient, such as the head of the patient.

As indicated above, health care professionals also use ex vivo devices that provide vascular cooling to a patient to reduce a patient's body temperature. For example, health care professionals typically utilize an ex vivo vascular cooling device during cardiovascular surgery. During cardiovascular surgery health care professionals perform a hypothermic bypass technique where blood is pumped from a patient, through a bedside machine that cools and oxygenates the blood, and back into the patient. The hypothermic bypass technique, however, typically requires the use of two vascular access catheters, a first vascular access catheter to remove blood from the patient and a second vascular access catheter to return blood to the patient. Both catheters typically require a long, circuitous ex vivo blood path to transport the blood from the subject to the bedside apparatus and back to the subject. The relatively long blood path results in a relatively large percentage of the volume of the patient's being located ex vivo. As the blood travels ex vivo through the blood line, the temperature of the blood changes as a result of a heat exchange between the walls of the blood line and the atmosphere. Heat transfer through the walls of the blood line of the blood path results in an increased difficulty in controlling the temperature of the blood returning to the patient. Also, because of the length of the blood line between the patient and the bedside machine the blood lines can be tripped over or otherwise dislodged, thereby causing the loss of a large amount of blood and injury to the patient.

By contrast, embodiments of the present invention significantly overcome such deficiencies and provide techniques for obtaining and then maintaining an optimal therapeutic temperature in the body of a patient. A fluid transfer assembly includes a fluid carrier, such as a catheter, and a heat exchange assembly coupled to the fluid carrier. The heat exchange assembly includes a heat exchange conduit, a heat exchanger in thermal communication with the heat exchange conduit, and a pump. The pump defines a stroke volume that is greater than a fluid carrier volume defined by the fluid carrier. The configuration of the stroke volume of the pump and the fluid carrier volume of the fluid carrier limits the length of the fluid carrier. In such a configuration, the heat exchange assembly orients in proximity to the body during operation to create a relatively short ex vivo flow path between a body and the heat exchange assembly. During operation, as the fluid flows along the ex vivo flow path, the relatively short ex vivo flow path minimizes thermal change in the fluid caused by a heat exchange between the walls of the fluid carrier and the atmosphere.

In one arrangement, the invention relates to a fluid transfer assembly having a fluid carrier and a heat exchange assembly. The fluid carrier defines a fluid carrier volume and has a distal end and a proximal end, the distal end configured to insert within a body lumen. The heat exchange assembly couples to the proximal end of the fluid carrier and has a heat exchange conduit in fluid communication with the fluid carrier, a heat exchanger in thermal communication with the heat exchange conduit, and a pump in fluid communication with the fluid carrier and in fluid communication with the at least one heat exchange conduit, the pump defining a stroke volume greater than the fluid carrier volume defined by the fluid carrier.

In another arrangement, the heat exchange conduit defines a heat exchange conduit volume greater than the stroke volume defined by the pump. Because the heat exchange conduit volume is greater than the stroke volume of the pump, fluid that enters the heat exchange conduit remains in thermal contact with the heat exchanger for a relatively long period of time or duration. Such time duration, therefore, allows efficient thermal adjustment (e.g., heating or cooling) of the fluid prior to the heat exchange assembly reintroducing the fluid to the patient.

In another arrangement, the heat exchange assembly has a fluid inlet check valve in fluid communication with the fluid carrier, in fluid communication with the pump, and in fluid communication with a fluid inlet of heat exchange conduit. The fluid inlet check valve is configured to engage a first position during a fluid intake stroke of the pump to direct a fluid from the fluid carrier to the pump. The fluid inlet check valve is also configured to engage a second position during a fluid output stroke of the pump to directing the fluid from the pump to the fluid inlet of the heat exchange conduit.

The fluid inlet check valve is formed from a flexible membrane that defines a substantially curved flow path between the pump and the fluid inlet of the heat exchange conduit when the fluid inlet check valve engages the second position during the fluid output stroke of the pump. The substantially curved flow path creates a hydrodynamic flow effect with respect to blood exiting the heat exchange assembly. The hydrodynamic flow effect maintains laminar flow within the fluid outlet path as the heat exchange assembly reintroduces thermally modified blood to a patient. Such laminar flow minimizes exposure of the red blood cells of the blood to relatively high shear stresses, thereby minimizing induction of hemolysis in the red blood cells.

In another arrangement, the heat exchange assembly has a fluid outlet check valve in fluid communication with the fluid carrier and in fluid communication with a fluid outlet of the heat exchange conduit. The fluid outlet check valve is configured to engage a first position during a fluid intake stroke of the pump, the first position of the fluid outlet check valve limiting entry of a fluid from the fluid carrier to the fluid outlet of the at least one heat exchange conduit. The fluid outlet check valve is also configured to engage a second position during a fluid output stroke of the pump, the second position of the fluid outlet check valve directing the fluid from the fluid outlet of the at least one heat exchange conduit to the fluid carrier.

The fluid outlet check valve is formed from a flexible membrane that defines a substantially curved flow path between the fluid outlet of the at least one heat exchange conduit and the fluid carrier when the fluid inlet check valve engages the second position during the fluid output stroke of the pump. The substantially curved flow path creates a hydrodynamic flow effect with respect to blood exiting the heat exchange assembly. The hydrodynamic flow effect maintains laminar flow within the fluid outlet path as the heat exchange assembly reintroduces thermally modified blood to a patient. Such laminar flow minimizes exposure of the red blood cells of the blood to relatively high shear stresses, thereby minimizing induction of hemolysis in the red blood cells.

In accordance with one aspect of this invention, an optimal therapeutic temperature is obtained and then maintained in a patient by placing a small caliber catheter into a blood vessel of the patient withdrawing a small quantity of blood from the patient through the catheter into a heat exchanger located ex vivo in close proximity to the patient, cooling or warming the blood within the heat exchanger, and returning the cooled or warmed blood to the patient through the catheter. Such a process is repeated in a continuous or cyclical manner to obtain an optimal therapeutic temperature in at least a portion of the patient.

In one arrangement, a user inserts a relatively small caliber, single lumen catheter into the blood vessel of the patient to obtain an optimal therapeutic temperature in the patient. For example, the user inserts the catheter into a carotid artery of the patient. Such a configuration allows selective induction of therapeutic hypothermia to the head of the patient. In one arrangement, a user inserts a relatively small caliber, multiple lumen catheter into the blood vessel of the patient to obtain an optimal therapeutic temperature in the patient.

In accordance with one aspect of this invention, an optimal therapeutic temperature is obtained and then maintained in a patient by placing a small caliber catheter into a blood vessel of the patient and attaching a temperature sensor to the body of the patient. A small quantity of blood is withdrawn from the patient through the catheter into a heat exchanger located ex vivo in close proximity to the patient, cooled or warmed within the heat exchanger, and returned to the patient through the catheter. The process is repeated in a continuous or cyclical manner where a control console is connected by umbilicals to the heat exchanger and the temperature sensor and where the process is controlled by mechanisms within the control console according to signals received from the temperature sensor.

In accordance with one aspect of this invention, therapeutic hypothermia is selectively induced in the head of a patient by inserting a small caliber catheter through the neck of the patient and into each common carotid artery, then withdrawing a small quantity of blood from the carotid arteries through the catheters into one common, or two separate heat exchangers, located ex vivo in close proximity to the neck of the patient, then cooling the blood within the heat exchangers, then returning the cooled blood to the carotid arteries through the catheters, and then repeating this process in a continuous or cyclical manner.

In accordance with one aspect of this invention, therapeutic hypothermia is selectively induced in the head of a patient by inserting at least one small caliber catheter through the neck of the patient and into at least one carotid artery, then withdrawing a small quantity of blood from the carotid arteries through the catheters into a heat exchangers located ex vivo in close proximity to the neck of the patient, then cooling the blood within the heat exchanger, then returning the cooled blood to the carotid artery through the catheter, and then repeating this process in a continuous or cyclical manner while simultaneously heating the body of the patient with a heating device.

One aspect of this invention relates to a patient temperature management system including a vascular access catheter having a distal end and a proximal end. The distal end is configured for placement into a blood vessel by common surgical technique and the proximal end of the catheter, located ex vivo during operation, has a vascular access port. The patient temperature management system also has an assembly including a heat exchanger and a blood pump, a control console, and an umbilical connecting the vascular access catheter to the control console. The control console and the vascular access catheter work in an operational relationship to remove blood from the patient, change the temperature of the blood removed from the patient, and reinsert the temperature alternated blood back into the patient. In one arrangement, the patient temperature management system has an emboli prevention system that either passively or actively minimizes or prevent emboli from entering the blood stream as a result of operation of the system.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Embodiments of the present invention provide techniques for obtaining and then maintaining an optimal therapeutic temperature in the body of a patient. A fluid transfer assembly includes a fluid carrier, such as a catheter, and a heat exchange assembly coupled to the fluid carrier. The heat exchange assembly includes a heat exchange conduit, a heat exchanger in thermal communication with the heat exchange conduit, and a pump. The pump defines a stroke volume that is greater than a fluid carrier volume defined by the fluid carrier. The configuration of the stroke volume of the pump and the fluid carrier volume of the fluid carrier limits the length of the fluid carrier. In such a configuration, the heat exchange assembly orients in proximity to the body during operation to create a relatively short ex vivo flow path between a body and the heat exchange assembly. During operation, as the fluid flows along the ex vivo flow path, the relatively short ex vivo flow path minimizes thermal change in the fluid caused by a heat exchange between the walls of the fluid carrier and the atmosphere.

Figure 1:
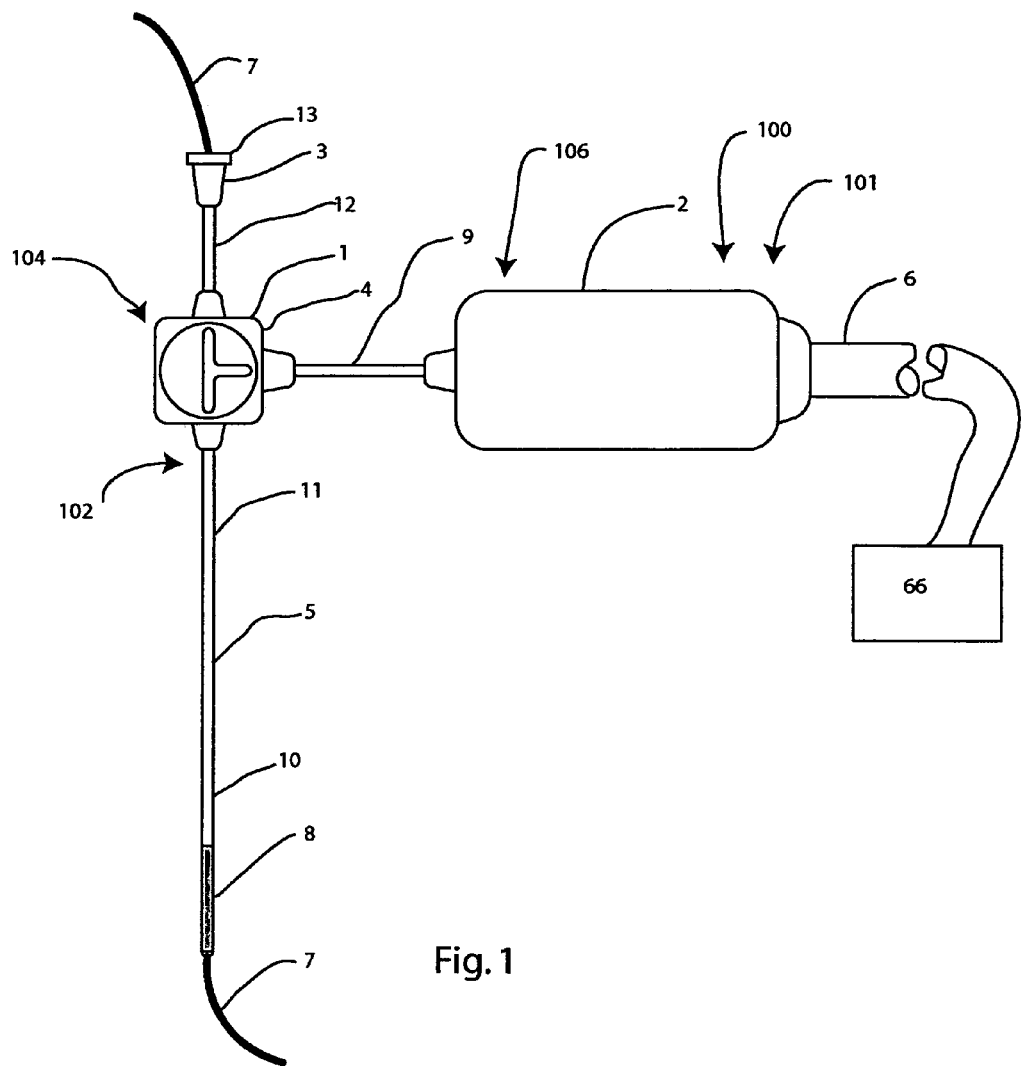
FIG. 1 illustrates a fluid transfer system, according to one embodiment of the invention.

FIG. 1 illustrates a fluid transfer assembly 100, according to one embodiment of the invention. The fluid transfer assembly 100 includes a fluid carrier 102, a heat exchange assembly 2. The fluid transfer assembly 100, in combination with a console 66 forms a fluid transfer system 101.

The fluid carrier 102 is formed from a catheter 1 having a catheter shaft 5, a stopcock 4, and a heat exchanger tube 9. The fluid carrier 102 is configured to insert within a body lumen, such as a lateral ventricle of a brain or a blood vessel, to carry fluid, such as cerebrospinal fluid or blood, respectively, both from the body lumen to the heat exchange assembly 2 and from the heat exchange assembly 2 to the body lumen.

The catheter shaft 5 is formed, for example, from an extrusion process using typical catheter materials such as nylon, polyethylene, or urethane. A manufacturer can incorporate glass fiber or metal wire into the walls of catheter shaft 5 to provide resistance to kinking or to provide torsional rigidity to the catheter 1.

In one arrangement, the catheter 1 is a single lumen vascular catheter 1 configured to insert within a blood vessel. For example, during an insertion procedure, a user (e.g., surgeon), by a standard surgical technique using an access needle (not shown) and guidewire 7, places a distal end 10 of vascular catheter through a puncture in the neck of the patient and either into a jugular vein or the superior vena cava. When positioned for operation, the distal end 10 resides in vivo in a major blood vessel, and a proximal end 11 of the catheter 1 remains ex vivo.

In one arrangement, the catheter 1 is configured to insert within a carotid artery of a body. For example, the catheter 1 has a relatively small caliber catheter shaft 5, thereby allowing insertion of the catheter 1 within relatively narrow blood vessels, such as the carotid artery, while minimizing obstruction of the blood flow through the blood vessels. In one arrangement, the catheter shaft 5 of the catheter 1 has an inner diameter between approximately 1 mm and 4 mm, a wall thickness between approximately 0.25 mm and 1.0 mm, and a length between approximately 10 cm and 20 cm. The outer diameter of the catheter shaft 5 of the catheter 1 is, therefore, between approximately 1.5 mm and 6 mm (between 4 French and 18 French).

In the case where the catheter 1 inserts within a blood vessel, use of the catheter 1 having an inner diameter between approximately 1 mm and 4 mm (e.g., the catheter 1 being between 4 French and 18 French) allows laminar flow of blood through the catheter 1 at a net flow rate of approximately 5 ml/sec through the catheter 1 (e.g., at a flow rate of 10 ml/second a fluid intake stroke of the heat exchange assembly 2 and at a flow rate of 10 ml/sec on a fluid output stroke of the heat exchange assembly 2). Such laminar (e.g., non-turbulent) flow minimizes exposure of the red blood cells of the blood to relatively high shear stresses, thereby minimizing induction of hemolysis in the red blood cells (e.g., a disintegration of the red blood cells forming the blood that causes a release of hemoglobin).

In one arrangement, the distal end 10 of the catheter has an emboli screen 8 to provide protection against (e.g., minimize) emboli from leaving vascular catheter 1 and entering a patient's blood stream during operation. The emboli screen 8, for example, is formed from a woven mesh of fine stainless steel wire coupled to the catheter, the mesh having interstices between approximately 250 and 1250 microns. In another example, the emboli screen 8 is integrally formed in the wall of catheter shaft 5, such as by perforations of between approximately 250 and 1250 microns in wall of the catheter 1 in the vicinity of distal end 10. In either example, the emboli screen 8 allows blood to flow into and out of catheter shaft 8 while capturing any emboli or clot that forms inside vascular catheter 1.

The stopcock 4 provides four-way fluid communication between the catheter 1, a vascular access port 3 and the heat exchange assembly 2, via the heat exchanger tube 9. The stopcock has a T-shaped actuator knob 14 that graphically represents a fluid path between the catheter 1, the vascular access port 3 and the heat exchange assembly 2 and through stopcock 4. With the stopcock 4 positioned as illustrated, the stopcock 4 provides fluid communication between the vascular access port 3, the catheter shaft 5 and the heat exchange assembly 2. With the stopcock 4 positioned 90 degrees clockwise of the position illustrated, the stopcock 4 provides fluid communication between the heat exchange 2 and the catheter shaft 5. With the stopcock 4 positioned 180 degrees clockwise of the position illustrated, the stopcock 4 provides fluid communication between the vascular access port 3 and the catheter shaft 5. With the stopcock 4 positioned 270 degrees clockwise of the position illustrated, the stopcock 4 provides fluid communication between the heat exchange assembly 2 and the vascular access port 3.

The vascular access port 3 has a vascular access port tube 12 and a female luer fitting 13. The vascular access port tube 12 defines an inner diameter of approximately 2 mm in diameter, defines an outside diameter of approximately 3 mm, and is between approximately 5 cm to 10 cm in length. The vascular access port tube 12, for example, is extruded from a variety of medical grade polymers including nylon and polyethylene. The vascular access port allows a user to infuse fluids (e.g., Ringer's solution, liquid medications) into a patient, sample blood (e.g., withdraw fluids) from the patient, monitor central venous pressure of the patient, and monitor central venous blood chemistry of the patient. The female luer fitting 13 provides a connection between a variety of standardized medical sensors, such as pressure monitors or blood gas analyzers, and a conventional connector associated with standardized fluid apparatuses such as connectors associated with blood bags, IV bags, infusion pumps, and syringes.

The heat exchanger tube 9 defines an inner diameter between 1 mm and 4 mm and is between approximately is 5 cm and 10 cm in length. The heat exchanger tube 9, for example, is extruded from various medical grade polymers such as nylon and polyethylene.

The stopcock 4, vascular access port 3, catheter 1, and heat exchanger tube 9, in one arrangement, act as a priming assembly 104 that introduces fluid into, and removes air from, the heat exchange assembly 2 prior to operation of the fluid transfer assembly 100. The priming assembly 104, therefore, minimizes the presence of air bubbles within the heat exchange assembly 2 to limit introduction of air bubbles into the blood vessel of a patient.

For example, during operation of the priming assembly 104, a user (e.g., surgeon), by standard surgical technique, inserts the distal end 10 of the vascular catheter 1 into a major blood vessel of a patient using an access needle and the guidewire 7. The user secures the vascular catheter 1 to the patient using a suture and retaining straps for example. After removing the guidewire 7 from the vascular catheter 1, the user rotates the stopcock 4 to a position 180 degrees clockwise from position shown and attaches a syringe to the vascular access port 3. The user withdraws blood from the patient into the syringe. The user then rotates the stopcock 4 to a position 270 degrees clockwise from the position shown and activates the heat exchange assembly 2 to pump blood between the syringe and the heat exchange assembly 2 until the heat exchange assembly 2 is primed with blood and all air is removed from the fluid path between the syringe and the heat exchange assembly 2 and within the heat exchange assembly 2.

The heat exchange assembly 2 of the fluid transfer assembly 100 includes a heat exchanger, a pump, and a sensor module and is described in detail below. The heat exchange assembly 2 couples to a proximal end 106 of the fluid carrier 102. The heat exchange assembly 2 also couples to the console 66 by way of an umbilical 6. The console 66 provides a thermal exchange fluid to the heat exchange assembly 2 to provide either a cooling or a warming of a body fluid extracted from a lumen of a patient. The console 66 also provides a pump actuating fluid to the pump of the heat exchange assembly, as described below. In such an arrangement, the umbilical 6 defines at least two heat exchange fluid conduits (e.g., a first heat exchange conduit to transfer heat exchange fluid to the heat exchange assembly 2 and a second heat exchange conduit to receive heat exchange fluid from the heat exchange assembly 2) and also defines two pump actuating fluid conduits (e.g., a first pump actuating fluid conduit to transfer pump actuating fluid to the heat exchange assembly 2 and a second pump actuating fluid to receive pump actuating fluid from the heat exchange assembly 2).

During operation, the heat exchange assembly 2 provides ex vivo warming or cooling of body fluid, such as a patient's blood, and returns the warmed or cooled blood to the patient. For example, assume a user (e.g., surgeon) has inserted the distal end 10 of the vascular catheter 1 into a major blood vessel of a patient and has primed the heat exchange assembly 2 using the priming assembly 104. To initiate an ex vivo thermal exchange process, for example, the user positions the stopcock 4 at a position 90 degrees clockwise from the orientation illustrated in FIG. 1. The pump of the heat exchange assembly 2 withdraws blood from the patient through the catheter shaft 5 and into the heat exchange assembly 2. The blood makes thermal contact with the heat exchanger of the heat exchange assembly to either heat or cool the blood. The pump of the heat exchange assembly 2 then returns the temperature altered blood back into the patient through catheter shaft 5. The heat exchange assembly repeats the process in a cyclical manner such that the heat exchange assembly removes blood from and reinserts blood into the patient at a rate of between approximately 50 and 400 ml/min. In one arrangement, the heat exchange assembly 2 reduces the temperature of the blood to between approximately 1° C. and 35° C. In another arrangement, the heat exchange assembly 2 increases the temperature of the blood between approximately 1° C. and 7° C. The amount of heat removed from or added to the patient is determined by the flow rate of the blood passing through the heat exchange 2 and the change in temperature of the blood within the heat exchange assembly 2.

As described, the fluid transfer assembly 100 provides ex vivo temperature alteration of a patient's body fluid and returns the temperature altered fluid to the patient. The fluid transfer assembly 100 allows a user to obtain, relatively rapidly, and then maintain an optimal therapeutic temperature in a patient. For example, the fluid transfer assembly 100 removes blood from a patient, lowers the temperature of the blood, and returns the cooled blood to the patient. Such a process induces a hypothermic state in a patient to minimize ischemic injury in the patient such as caused when the patient suffers from a stroke, cardiac arrest, heart attack, or trauma.

The fluid transfer assembly 100 includes a catheter 1 configured to insert into a blood vessel of a patient and to couple to the heat exchange assembly 2. In such an arrangement of the fluid transfer assembly 100, a user (e.g., surgeon) inserts the catheter 1 into a blood vessel of a patient using conventional surgical techniques (e.g., insertion of the catheter into a blood vessel of a patient does not require specialized intra-vascular procedural skill of the user). The catheter allows the surgeon to provide thermal management (e.g., heating or cooling) of a patient's blood while minimizing or eliminating the use of radiographic imaging techniques (e.g., advanced imaging equipment) to ensure proper alignment or orientation of the catheter 1 within the blood vessel of the patient.

As indicated above, the catheter 1 has a relatively small caliber catheter shaft 5. Use of such a relatively small caliber catheter shaft 5 allows a user to insert the catheter 1 within a carotid artery of a patient while minimizing obstruction of blood flow within the carotid artery. Placement of the catheter 1 within the carotid artery of the patient allows the heat exchange assembly 2 to substantially isolate cooling of the patient to the patient's head (e.g., to selectively cool the head of the patient), for example. During selective head cooling, relatively low hypothermic temperatures are achieved in the brain, compared to conventional systemic hypothermic induction devices, because the patient's head and not the entire patient's body, is exposed to hypothermia. Also, by selectively cooling the head using the fluid transfer assembly 100, hypothermia therapy can be applied relatively rapidly in the brain, compared to conventional systemic hypothermic induction devices, since the fluid transfer assembly 100 provides cooling to only the head of the patient, rather than the patient's entire body. Furthermore, by inducing localized hypothermia via selective head cooling, a user can maintain hypothermic temperatures within the brain for a relatively long time interval while minimizing systemic complications of inducing systemic hypothermia in a patient and while minimizing the creation of significant temperature gradients within the brain.

Selective cooling of a patient head allows a user to induce a hypothermic condition in the head of the patient in the case where the patient has experienced a spinal cord injury in the upper vertebral area. By selectively cooling the head in such a case, users (e.g., surgeons) can treat the patient's spinal chord injuries with hypothermia at a relatively greater depth and duration compared to induction of conventional systemic hypothermia. Selective cooling of a patient head, through the use of a catheter inserted within a carotid artery of a patient, also allows the user to induce a hypothermic condition in the head of the patient in the case where the patient has suffered a stroke, head trauma, subarachnoid hemorrhage, or brain hemorrhage, or in the time period during or following a surgical procedure.

FIG. 2 illustrates an arrangement of the fluid transfer assembly 100, according to another embodiment of the invention. The fluid transfer assembly 100 includes a fluid carrier 102 having a multiple lumen vascular catheter 15 defining catheter shaft 18, a stopcock 17, and a multiple lumen heat exchanger tube 20. The fluid transfer assembly 100 also includes a heat exchange assembly 16 coupled to the catheter 15 via the multiple lumen heat exchanger tube 20.

Figures 2A, 2B, 2C:
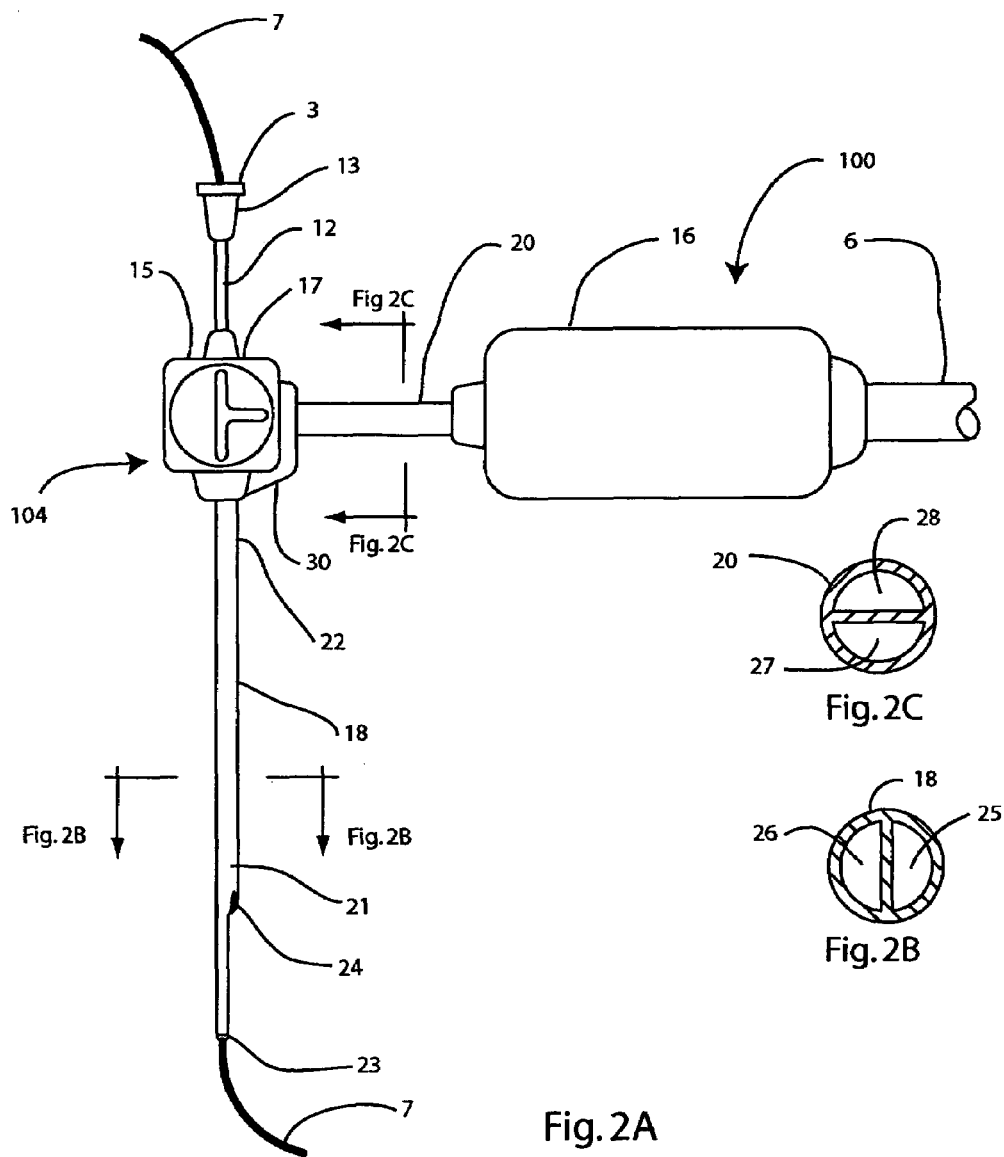
FIG. 2A illustrates a fluid transfer system having a multiple-lumen vascular catheter, according to one embodiment of the invention.
FIG. 2B illustrates a sectional view of the heat exchanger tube of FIG. 2A.
FIG. 2C illustrates a sectional view of the catheter shaft of FIG. 2A.
Figure 3A:
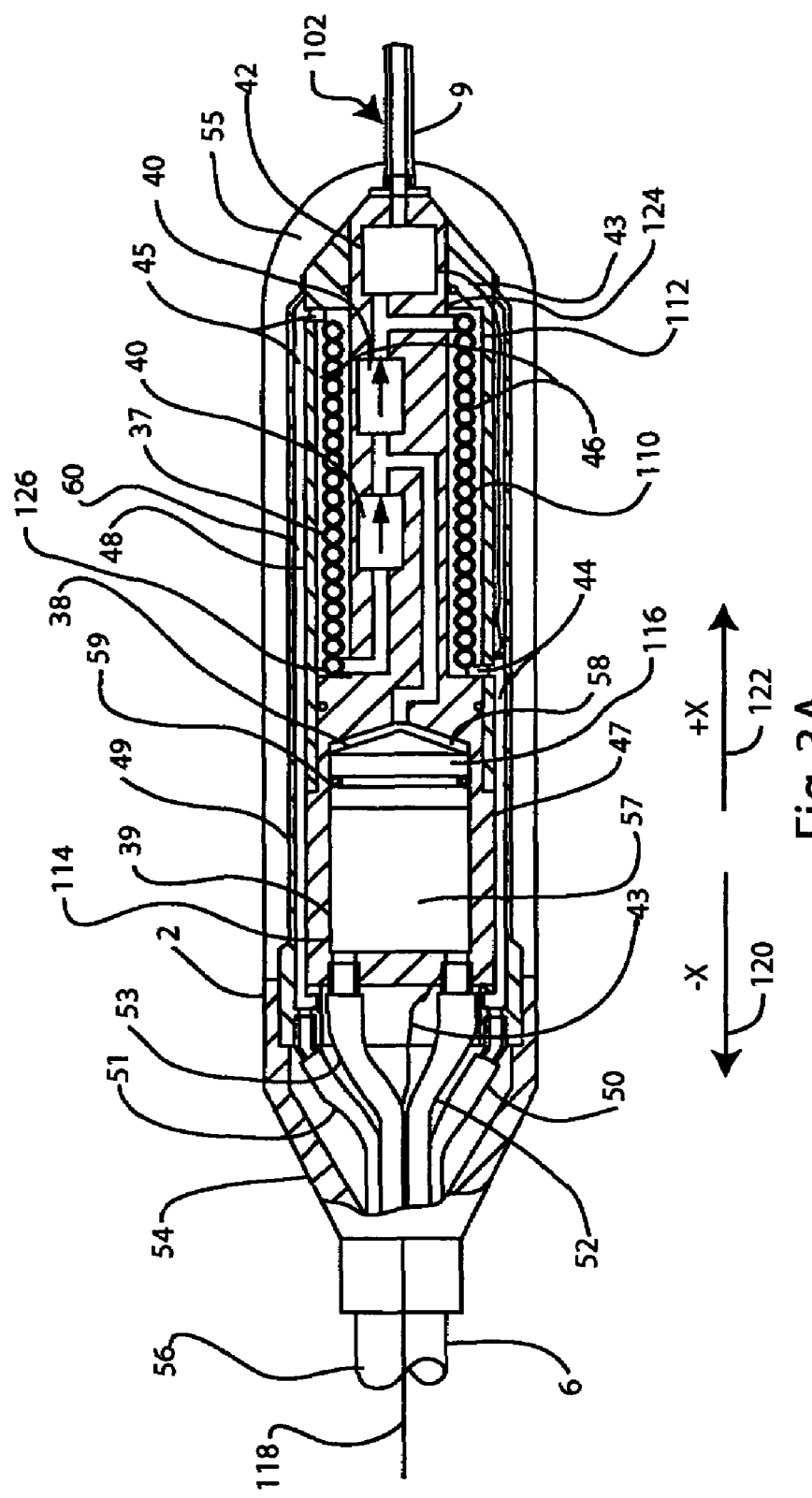
FIG. 3A illustrates a first sectional view of the heat exchange assembly of FIG. 1, according to one embodiment of the invention.
Figure 3B:
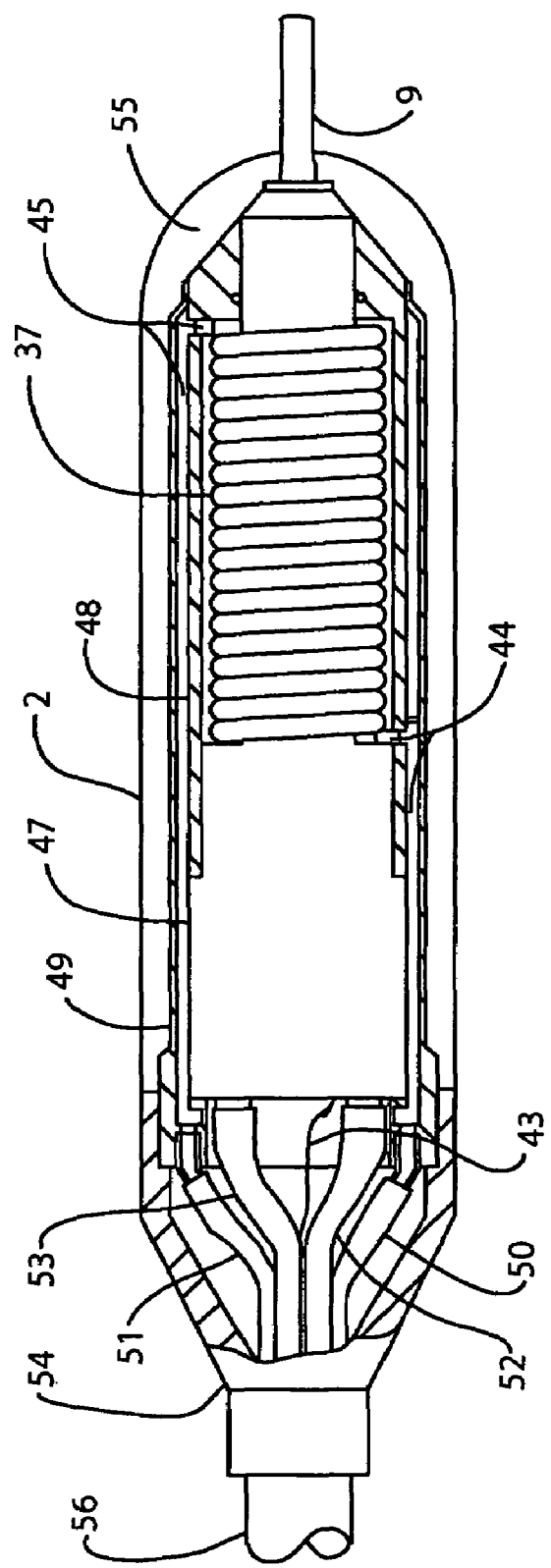
FIG. 3B illustrates a second sectional view of the heat exchange assembly of FIG. 1, according to one embodiment of the invention.
Figure 3C:
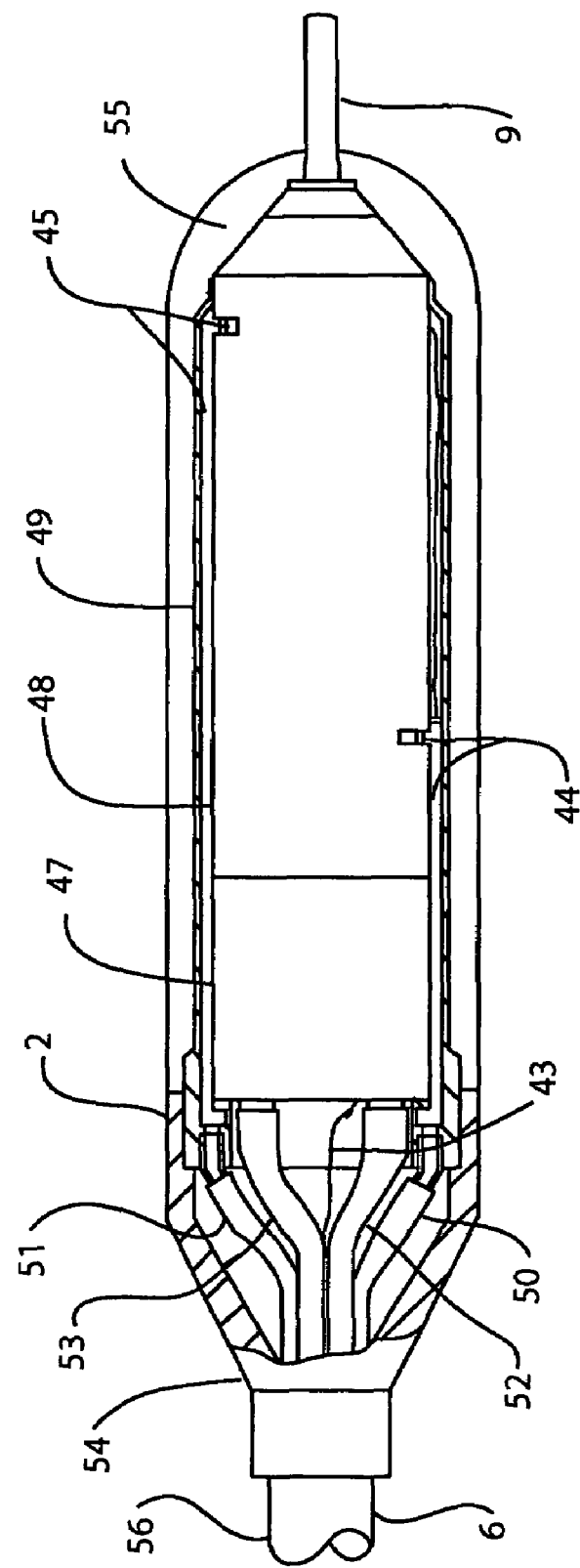
FIG. 3C illustrates a third sectional view of the heat exchange assembly of FIG. 1, according to one embodiment of the invention.
Figure 3D:
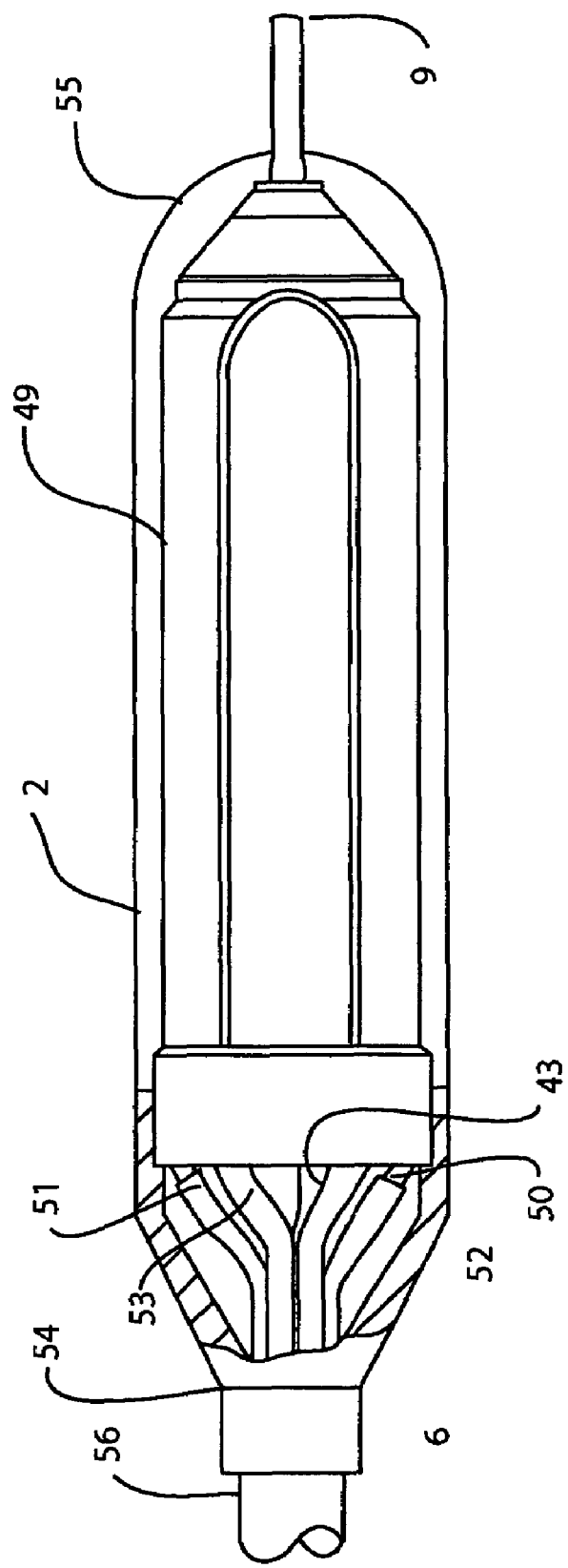
FIG. 3D illustrates a fourth sectional view of the heat exchange assembly of FIG. 1, according to one embodiment of the invention.

The catheter shaft 18 has an outer diameter between approximately 2 mm and 5 mm and has a wall thickness between approximately 0.25 mm and 1.0 mm. In one arrangement, the catheter shaft 18 defines two lumens: a blood inlet lumen 25 and a blood outlet/guidewire lumen 26. FIG. 2B illustrates a cross-sectional view of the catheter shaft 18. The multiple lumen heat exchanger tube 20, in one arrangement, also defines two lumens: inlet lumen 27 and outlet lumen 28. FIG. 2C illustrates a cross-sectional view of the multiple lumen heat exchanger tube 20.

The stopcock 17 provides four-way fluid communication between the vascular access port 3, the blood outlet/guidewire lumen 26 of catheter shaft 18, and the heat exchanger tube outlet lumen 28. The T-shaped actuator knob 29 is graphically indicative of the fluid path through stopcock 17. With the stopcock 17 positioned as illustrated, the stopcock 17 provides fluid communication between the vascular access port 3, the outlet lumen 28 of heat exchanger tube 20, and the blood outlet/guidewire lumen 26 of catheter shaft 18. With the stopcock 17 positioned 90 degrees clockwise of the position illustrated, the stopcock 17 provides fluid communication between the outlet lumen 28 of the heat exchanger tube 20 and the blood outlet/guidewire lumen 26 of the catheter shaft 18. With stopcock 17 positioned 180 degrees clockwise of the position illustrated, the stopcock 17 provides fluid communication between the vascular access port 3 and the blood outlet/guidewire lumen 26 of the catheter shaft 18. With the stopcock 17 positioned 270 degrees clockwise of the position illustrated, the stopcock 17 provides fluid communication between the outlet lumen 28 of heat exchanger tube 20 and the vascular access port 3. The stopcock 17 also defines a fixed fluid path through a boss 30 of the stopcock 17 where the fixed fluid path that allows fluid communication between the inlet lumen 27 of the heat exchanger tube 20 and the inlet lumen 25 of the catheter shaft 18.

The stopcock 17, vascular access port 3, catheter 15, and heat exchanger tube 20, in one arrangement, act as a priming assembly 104 that introduces fluid into, and removes air from, the heat exchange assembly 16 prior to operation of the fluid transfer assembly 100. For example, during operation of the priming assembly 104, a user inserts a distal end 21 of the two-lumen vascular catheter 15 into a major blood vessel of a patient using an access needle and guidewire 7 by standard surgical technique. The user secures the two-lumen vascular catheter 15 to the patient using suture and retaining straps, for example. The user removes the guidewire 7 from the two-lumen vascular catheter 15 (e.g., from the blood outlet/guidewire lumen 26 of the catheter 15). The user positions the stopcock 17 at an orientation 180 degrees from the position illustrated and attaches a syringe to the vascular access port 3. The user withdraws blood from the patient, through blood outlet/guidewire lumen 26, by withdrawing a plunger of the syringe. The user positions the stopcock 17 at an orientation 270 degrees clockwise from the position shown and activates the system 100. The system 100 pumps blood from the patient through fluid inlet lumen 25, though fluid path in the boss 30, through the inlet lumen 27, though the heat exchanger/pump assembly 16, though the outlet lumen 28, through the stopcock 17, through the vascular access port 3 and into the syringe until all air is cleared from the fluid path between the patient and the syringe.

Once the user has primed the heat exchange assembly 16, the heat exchanger tube 20, and the catheter 18, the user positions the stopcock 17 at an orientation 90 degrees clockwise from position illustrated (e.g., the operational position). During operation of the fluid transfer system 100, the heat exchange assembly 16 withdraws blood from the patient into a blood inlet port 24 defined by the catheter 1. From the inlet port 24, the blood travels through the lumen 25 defined by the catheter 18, through the fluid path in the boss 30, through the inlet lumen 27 of the heat exchanger tube 20, and into heat exchange assembly 16. The blood makes thermal contact with a heat exchanger of the heat exchange assembly 16 to either heat (e.g., increase in temperature between approximately 1° C. and 7° C.) or cool (e.g., reduce in temperature between approximately 1° C. and 35° C.) the blood. The heat exchange assembly 16 returns the temperature altered blood back into the patient through the outlet lumen 28 of the heat exchanger tube 20, the stopcock 17, the blood outlet/guidewire lumen 26 of the catheter 18, and through a blood outlet port 23 defined by the catheter 18. The heat exchange assembly 16 performs such a process in a cyclical or continuous manner where blood is removed from and then reinserted back into the patient at a rate of between approximately 50 and 400 ml/min.

FIGS. 3A through 3D illustrate sectional views of the heat exchange assembly 2, according to one embodiment of the invention. The heat exchange assembly 2 (not including the umbilical 6) has a length between approximately 10 m and 15 cm and has an outer diameter of between approximately 3 cm and 4 cm. As illustrated, the heat exchange assembly 2 has a heat exchanger housing 48 either machined from a surgical grade stainless steel or molded from a medical grade polymer, for example. The heat exchanger housing 48 houses a heat exchange conduit 110 and a heat exchanger 112. The heat exchange assembly 2 also includes a pump 114 having a pump housing 47 and an actuator 118 in communication with the housing 47, a sensor module 42, a first check valve 40, and a second check valve 41.

The heat exchange conduit 110 within the heat exchanger housing 48 is configured to receive fluid (e.g., blood) from a patient via the fluid carrier (e.g., heat exchanger tube 9). In one arrangement, the heat exchange conduit 110 is configured as a heat exchanger coil 37 where the heat exchange conduit 110 forms a coil-shaped conduit relative to a central axis 118 defined by the heat exchange assembly 2. The heat exchanger coil 37 is formed, for example, from stainless steel hypodermic tubing.

The heat exchanger 112 is configured to circulate a heat exchange fluid, such as water, saline, or another suitable liquid, in proximity to the heat exchange conduit 110. For example, in one arrangement, the heat exchanger 112 is configured as a heat exchange fluid chamber 46 that surrounds the heat exchange conduit 110. In one arrangement, a pump housing 47 and a heat exchanger housing 48 defines the heat exchange fluid chamber 46. The heat exchange fluid chamber 46 couples to a heat exchange fluid housing 49 of the heat exchange assembly 2. In one arrangement, the heat exchange fluid housing 49 is machined from a surgical grade stainless steel or molded from a medical grade polymer. The heat exchange fluid housing 49 defines a heat exchange fluid inlet channel 44 in fluid communication with a heat exchange fluid inlet tube 50 and defines a heat exchange fluid outlet channel 45 in fluid communication with a heat exchange fluid outlet tube 51. In one arrangement, the tubes 50 and 51 are formed from tygon tubing having an inner diameter of between approximately 0.125 and 0.25 inches.

The heat exchange conduit 110 works in conjunction with the heat exchanger 112 to either heat or cool fluid received by the heat exchange conduit 110 via the fluid carrier 102. For example, during operation, the control console 66 pumps a heat or thermal exchange fluid through the umbilical 6 to the heat exchange fluid inlet tube 50 of the heat exchange assembly 2. The heat exchange fluid travels from the heat exchange fluid inlet channel 44, into the heat exchange fluid chamber 46 into the heat exchange fluid outlet channel 45, and back to control console 66 through the heat exchange fluid outlet tube 51. As the thermal exchange fluid contacts the heat exchange conduit 110, heat is exchanged between fluid within heat exchange conduit 110 and the thermal exchange fluid, thereby altering the temperature of the fluid within heat exchange conduit 110. For example, in patient warming mode the console 66 provides heat exchange fluid to the heat exchange assembly 2 at a temperature between approximately 40° C. and 60° C. while, in patient cooling mode the console 66 provides heat exchange fluid to the heat exchange assembly 2 at a temperature between approximately 0° C. and 30° C.

The pump, in one arrangement, is formed from a pump cylinder 39 machined in pump housing 47. The pump housing 47 can be machined out of surgical grade stainless steel or molded from a medical grade polymer. The pump 114 is configured to cycle fluid (e.g., blood) between the heat exchange assembly 2 and a patient. For example, as the actuator 116 moves from a first position (as shown) to a second position along a −X direction 120 (e.g., from right to left), the pump 114 withdraws fluid from the patient into heat exchanger/pump assembly 2 (e.g., the pump 114 undergoes a fluid intake stroke). As the actuator 116 moves from the second position back to the first position along a +X direction 122 (e.g., from left to right), the pump 114 returns the fluid from heat exchange assembly 2 to the patient (e.g., the pump 114 undergoes a fluid output stroke).

The pump 114 is configured with pump tubes 52 and 53 (e.g., pump suction tube 52 and pump pressure tube 53) that provide fluid communication between the pump 114 and the control console 66 via the umbilical 6. In one arrangement, the tubes 52 and 53 are formed from tygon tubing having an inner diameter of between 0.125 and 0.25 inches. During operation, the console 66 introduces fluid into the pump 114 (e.g., into an actuation chamber 57 defined by the pump housing 47 and the actuator 116) via pump tube 53 to cause the pump 114 to undergo a fluid output stroke (e.g., cause the actuator 116 to displace along the +X direction). The console 66 then removes fluid from the pump 114 (e.g., from the actuation chamber 57 defined by the pump housing 47 and the actuator 116) via pump tube 52 to cause the pump 114 to undergo a fluid intake stroke (e.g., cause the actuator 116 to displace along the −X direction). In one embodiment, the fluid used to actuate the actuator 116 is a liquid. Because liquid is not compressible, a sudden stoppage of flow of liquid from the control console 66 to the actuation chamber 57 (e.g., such as caused by a kink developing in the umbilical 6) results in the immediate stoppage in movement of the actuator 116 (e.g., piston 38). By minimizing a delay in stopping the movement of the actuator 116 and increase the probability that an embolus enters the patient's blood stream without being detected (e.g., detected by the sensor 42).

In one arrangement, the pump 114 includes a pump piston 38 (e.g., actuator 116) within the pump housing 47. The pump piston 38, for example, is machined from a surgical grade stainless steel or molded from medical grade polymer. In one arrangement, the piston 38 has a piston seal 59, such as an elastomer o-ring, oriented between the piston 38 and the housing 47.

The pump 114 defines a stroke volume, illustrated by the actuation chamber 57, defined by the pump housing 47 and the actuator 116 where the stroke volume of the pump 114 is greater than a fluid carrier volume defined by the fluid carrier 102. In one arrangement, the fluid carrier volume of the fluid carrier 102 (e.g., the volume of the blood contained in a blood path between the distal end 10 of catheter shaft 5 and the heat exchange assembly 2) is less than approximately 20% of the stroke volume (e.g., displacement of the pump piston 38) within the heat exchange assembly 2. In another arrangement, the fluid carrier volume of the fluid carrier 102 is less than approximately 25% of the stroke volume within the heat exchange assembly 2. In another arrangement, the fluid carrier volume of the fluid carrier 102 is less than between approximately 30% and 60% of the stroke volume of the pump within the heat exchange assembly 2.

The stroke volume is defined as an amount of fluid that the pump 114 either withdraws from a patient or returns to the patient during a single actuator actuation (e.g., during a fluid intake stroke or during a fluid output stroke). The fluid carrier volume represents the fluid volume capacity of the fluid carrier 102. For example, as illustrated in FIG. 1 above, the fluid carrier 102 includes the catheter 1, the stopcock 4, and the heat exchanger tube 9. The fluid carrier volume of the fluid carrier 102, with respect to FIG. 1, is equal to the total volumetric fluid capacity of (e.g., the volume of fluid capable of containment by) the catheter 1, the stopcock 4, and the heat exchanger tube 9. Such total volumetric fluid capacity is less than the stroke volume of the pump.

With the stroke volume of the pump 114 greater than the fluid carrier volume of the fluid carrier 102, the heat exchange assembly 2 allows delivery of an amount of thermally adjusted fluid (e.g., fluid exposed to the heat exchanger 112 of the heat exchange assembly 112), such as blood previously removed from the patient, sufficient to induce a thermal condition (e.g., hypothermia) in at least a portion of the patient. For example, assume the pump 114 defines a stroke volume of 10 ml per actuator stroke and the fluid carrier 102 defines a fluid carrier volume of 3 ml. During operation, as the pump 114 performs a fluid intake stroke, at the peak of the stroke (e.g., the actuation chamber 57 being filled with fluid, such as blood) the fluid carrier 102 contains 3 ml of fluid that is not exposed to the heat exchanger 112 of the heat exchange assembly 2. As the pump 114 performs a fluid output stroke, the pump 114 displaces 10 ml of thermally adjusted fluid through the fluid carrier 102, dispersing the 3 ml of fluid held within the fluid carrier in addition to approximately 7 ml of thermally adjusted fluid. In such a case, the patient receives a net amount of 4 ml thermally adjusted fluid. In such a configuration of the stroke volume of the pump 114 and the fluid carrier volume of the fluid carrier 102, during a fluid output stroke the patient receives a greater amount of thermally adjusted fluid (e.g., fluid exposed to the heat exchanger) than non-thermally adjusted fluid (e.g., fluid held within the fluid carrier 102 after a fluid input stroke). The configuration of the stroke volume of the pump 114 and the fluid carrier volume of the fluid carrier 102, therefore, provides heating or cooling of the patient.

Furthermore, in the configuration where the stroke volume of the pump 114 is greater than the fluid carrier volume of the fluid carrier 102, a method for minimizing the fluid carrier volume involves minimizing a distance between a distal end of the fluid carrier 102 (e.g., a distal end 10 of the catheter 1) and the proximal end 106 of the fluid carrier 102. By minimizing such a distance between the heat exchange assembly 2 and the patient, the heat exchange assembly 2 orients in relatively close proximity to the patient. With the heat exchange assembly 2 oriented in proximity to the patient, such an orientation limits a user (e.g., surgeon or heath care worker) from accidentally disconnecting the fluid carrier 102 from the heat exchange assembly 2 during operation, such as typically caused by a user tripping over a fluid carrier 102 attached between a patient and a heat exchanger located at a distance from the patient.

As indicated above, the heat exchange assembly 102 includes a first check valve 40 and a second check valve 41. The first check valve 40 orients in fluid communication with the fluid carrier 102, in fluid communication with the pump 116, and in fluid communication with a fluid inlet 124 the heat exchange conduit 110. The second check valve 41 orients in fluid communication with the pump 114 and in fluid communication with a fluid outlet 126 of the heat exchange conduit 110.

During operation of the heat exchange assembly 2, the console 66 actuates the actuator 116 along the −X direction 120 (e.g., performs a fluid intake stroke) to withdraw blood from a patient into the heat exchange assembly 2. During the fluid intake stroke, the first check valve 40 engages a first position (e.g., closed position) to direct the blood from the fluid carrier 102 (e.g., heat exchanger tube 9) to the fluid inlet 124 of the heat exchange conduit 110. The blood travels through the heat exchange conduit 110, exits the fluid outlet 126 of the heat exchange conduit 110, and flows into the second check valve 41. Such flow causing the second check valve 41 to engage a first position (e.g., open position) and direct the blood from the fluid outlet 126 to the pump 114 (e.g., into the chamber 58 of the pump 114).

Also during operation of the heat exchange assembly 2, the console 66 actuates the actuator 116 along the +X direction 122 (e.g., performs a fluid output stroke) to transmit blood (e.g., thermally modified blood) from the heat exchange assembly 2 and into the patient. During the fluid output stroke, the second check valve 41 engages a second position (e.g., a closed position) that limits or prevents entry of the fluid from the pump 114 (e.g., from the chamber 58 of the pump 114) to the fluid outlet 126 of the heat exchange conduit 110. The second check valve 41 directs the fluid toward the first check valve 40. In response to receiving the fluid during the fluid output stroke, the first check valve 40 engages a second position (e.g., open position) that directs the fluid from the pump 114 to the fluid carrier 102.

The use of the first check valve 40 and the second check valve 41 creates a fluid inlet flowpath (e.g., through the heat exchange conduit 110, through the second check valve 41, and into the chamber 57 defined by the pump 114) and a separate fluid outlet flowpath (e.g., from the chamber 57 defined by the pump 114, through the first check valve 40, and into the fluid carrier 102). Such a configuration allows the volume of the fluid inlet flowpath to be different from the volume of the fluid outlet flowpath. In one arrangement, heat exchange conduit 110 defines a heat exchange conduit volume where the heat exchange conduit volume is greater than the stroke volume defined by the pump 114. In such an arrangement, the volume of the fluid inlet flowpath (e.g., the heat exchange conduit 110) is greater than the volume of the fluid outlet flowpath (e.g., the stroke volume of the pump 114).

For example, assume fluid enters the heat exchange conduit 110 from the fluid carrier 102 at Time A. With the heat exchange conduit volume is greater than the stroke volume of the pump 114, the actuator 116 of the pump 114 actuates over several cycles (e.g., several fluid input strokes and several corresponding fluid output strokes) before the fluid that entered the heat exchange conduit 110 at Time A enters the chamber 57 defined by the pump 114. As the actuator 116 actuates, the fluid moves through the heat exchange conduit 110 and thermally communicates with the heat exchange fluid chamber 46 surrounding the heat exchange conduit 110. Because the heat exchange conduit volume is greater than the stroke volume of the pump 114, the fluid that enters the heat exchange conduit 110 remains in thermal contact with the heat exchange fluid chamber 46 for a relatively long period of time or duration. Such time duration, therefore, allows efficient thermal adjustment (e.g., heating or cooling) of the fluid prior to the heat exchange assembly 2 reintroducing the fluid to the patient.

The displacement of the actuator 116 of the pump 114 and a length of the heat exchange conduit 110 can vary according to the clinical application. For example, for selective head cooling using two carotid artery catheters, a pump displacement of 1 ml to 3 ml and a heat exchange conduit 110 with the conduit having an inner diameter of 1.5 mm to 2.5 mm and a path length of approximately 0.4 to 1.0 meters provides a volume of thermally adjusted fluid to a patient sufficient to induce a thermal change in the patient. In another example, for whole body temperature management using a single central venous catheter, a pump displacement approximately of 3 ml to 10 ml, a heat exchange conduit 110 with the conduit having an inner diameter of approximately 3.0 mm to 5 mm, and a path length of between approximately 0.75 and 2.0 meters is sufficient to induce a thermal change in the patient.

In one arrangement, the heat exchange assembly 2 has a sensor module 42 (e.g., sensor) in fluid communication with the fluid carrier 102. In one arrangement, the sensor 42 is configured as a temperature sensor. For example, the temperature sensor is formed of a thermistor or a thermocouple that measures the temperature of fluid (e.g., blood) flowing into or from the heat exchange assembly 2. In another arrangement, the sensor 42 is configured as a blood flow rate sensor. For example, the blood flow rate sensor is formed from a thermistor. In another arrangement, the sensor 42 is configured as a bubble detection sensor. For example, the bubble detection sensor is formed from an optical emitter and receiver or an ultrasonic detector. In another arrangement, the sensor 42 is configured as a clot detection sensor formed from an optical emitter and receiver or from an ultrasonic detector.

The sensor 42 couples to the console 66 via a sensor module lead 43. The sensor module 42 transmits electrical signals indicative of blood temperature, blood flow rate, or the presence of emboli (e.g., bubbles or clots) within the blood to the control console 66. The console 66 uses these signals to control the rate at which the pump 114 is actuated, the temperature and flow rate of heat transfer fluid through heat exchange assembly 2, or the detection of any out of parameter operation for the actuation of safety interlocks associated with the fluid transfer assembly 100 (e.g., e.g., where the interlocks prevent operation of the system 101 if the user does not operate the system 101 correctly or if the system 101 malfunctions). The console 66 uses the signal indicating the presence of emboli to detect the presence of emboli within heat exchanger assembly 2 and to trigger an immediate stoppage of the pump 114. In such an arrangement (e.g., when the sensor 42 is configured as a bubble detection sensor), the console 66 and sensor form an emboli prevention system.

In one arrangement, the heat exchange assembly 2 has a strain relief 54, an insulation cover 55, and an umbilical sheath 56 configured to cover a connector located on a connection end of the umbilical 6. The strain relief 54 provides "give" to the heat exchange assembly 2 to allow a user to distend the umbilical 6 of the fluid transfer assembly 100 while minimizing potential detachment of the umbilical 6 from the heat exchange assembly 2. For example, the strain relief is molded from a flexible polymer and is assembled to umbilical sheath 56 and heat exchange fluid housing 49 as shown. The insulation cover 55 aids in maintaining a temperature within the heat exchange assembly 2. For example, the insulation cover 55 is a closed cell foam rubber configured to mold about the assembly 2 as shown.

Figure 4:
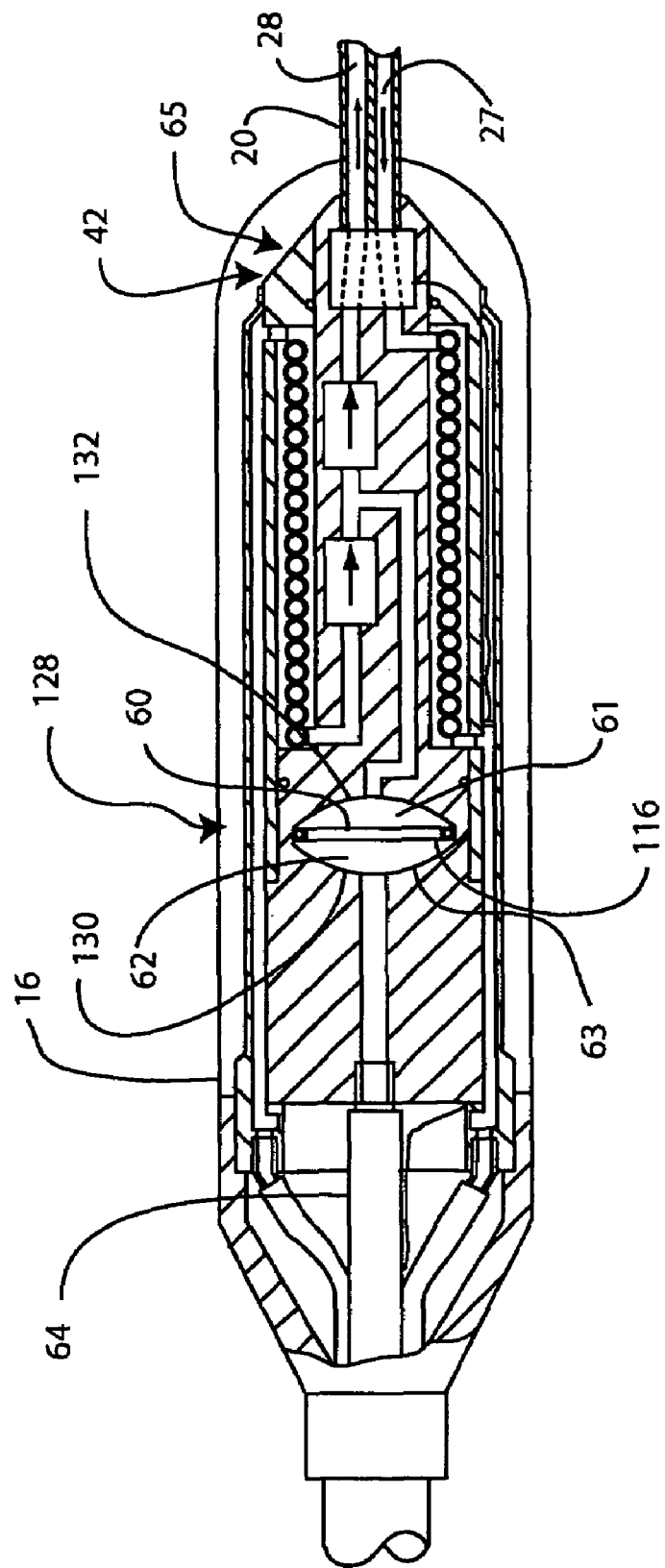
FIG. 4 illustrates a sectional view of a heat exchange assembly for use with the fluid transfer system of FIG. 2, according to one embodiment of the invention.

FIG. 4 illustrates a sectional view of an embodiment of an ex vivo heat exchange assembly 16. The heat exchange assembly 16 has a pump 114 configured as a diaphragm pump 128. The diaphragm pump 128 includes a diaphragm 60 disposed within a diaphragm pump cavity 63 that defines a diaphragm actuation chamber 62. The diaphragm 60 is formed from an elastomeric membrane that divides the diaphragm pump cavity 63 into the diaphragm actuation chamber 62 and a diaphragm fluid chamber 61. When the control consol 66 applies a negative pressure to the diaphragm actuation chamber 62, the diaphragm 60 displaces against a first (e.g., left) wall 130 of the diaphragm pump chamber 63 to draw blood from the patient into the diaphragm blood chamber 61. When the control consol 66 applies a positive pressure to the diaphragm actuation chamber 62, the diaphragm 60 displaces against a second (e.g., right) wall 132 of diaphragm pump chamber 63 to push blood out of diaphragm blood chamber 61 and back into the patient. The displacement of the diaphragm pump is between approximately 0.25 ml and 2.0 ml, for example, and the rate of pumping is between 1 and 10 Hertz (Hz).

FIG. 4 illustrates a sectional view of an embodiment of an ex vivo heat exchange assembly 16 having a two lumen (e.g., double lumen) catheter 15. The double-lumen catheter 15 defines a first lumen 27 and a second lumen 28. Operation of the heat exchange assembly 16 is similar to the operation of the heat exchange assembly 2 described above. During operation, the double-lumen catheter 15 provides fluid, via the first lumen 27, from a body lumen of a patient, such as a blood vessel, to the heat exchange assembly 16 during a fluid intake stroke of the actuator 116 of the pump 128. The double-lumen catheter 15 also delivers fluid, via the second lumen 28, from the heat exchange assembly 16 and to a body lumen during a fluid output stroke of the actuator 116 of the pump 128. The sensor module 65 operates in the same manner as sensor module 42 illustrated in FIG. 3A, however, the sensor module 42 provides two separate blood conduits. In one arrangement, the sensor module provides two sets of sensors, one for each conduit.

Figure 5:
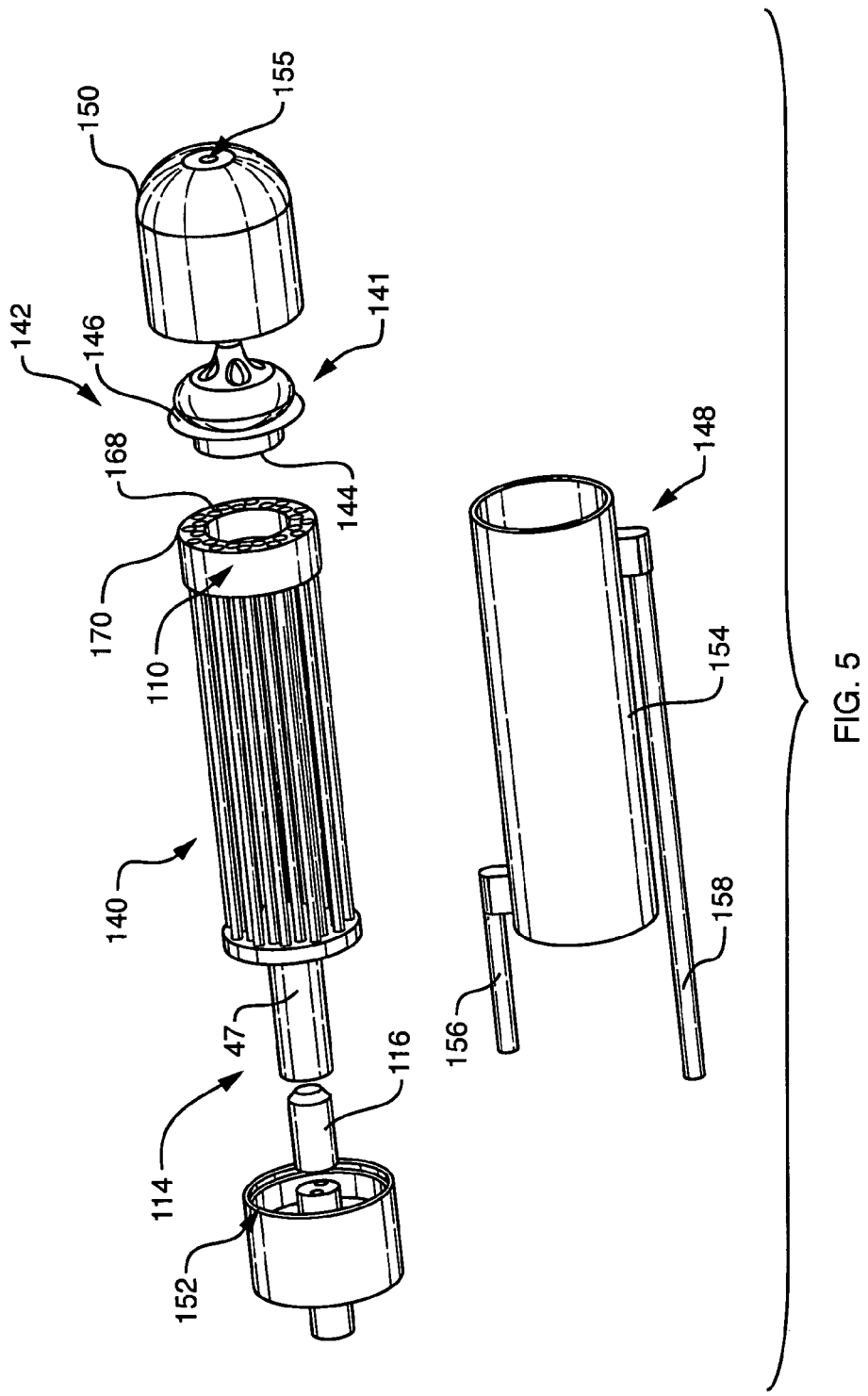
FIG. 5 illustrates an exploded view of a heat exchange assembly, according to another embodiment of the invention.

FIGS. 5 and illustrates an arrangement of a heat exchange assembly 140 according to another embodiment of the invention. The heat exchange assembly 140 has a heat exchange conduit 110, a pump 114 having an actuator 117 and a housing 47, and a check valve assembly 142. The heat exchange assembly 140 also has a heat exchange housing 148 that includes a proximal covering 150, a distal covering 152 and a heat exchange conduit covering 154.

The heat exchange conduit covering 154 is configured to surround the heat exchange conduit 110 and circulate thermal exchange fluid about the heat exchange conduit 110. The heat exchange conduit covering 154 has a thermal exchange fluid inlet 156 and thermal exchange fluid outlet 158, the inlet 156 and outlet 158 configured to couple to the console 66. During operation, the console 66 pumps thermal exchange fluid into the thermal exchange fluid inlet 156 of the heat exchange conduit covering 154 and receives the thermal exchange fluid from the thermal exchange fluid outlet 158.

In one arrangement, the heat exchange conduit 110 of the heat exchange assembly 140 has twelve separate heat exchange conduits 160, each conduit 160 having a corresponding fluid inlet conduit 160 and fluid outlet conduit 164. Such a configuration provides sufficient surface area of the heat exchange conduit 110 in thermal communication with a thermal exchange fluid contained within the heat exchange conduit covering 154, therefore allowing heating or cooling of the fluid within the heat exchange conduit 110.

Figure 6:
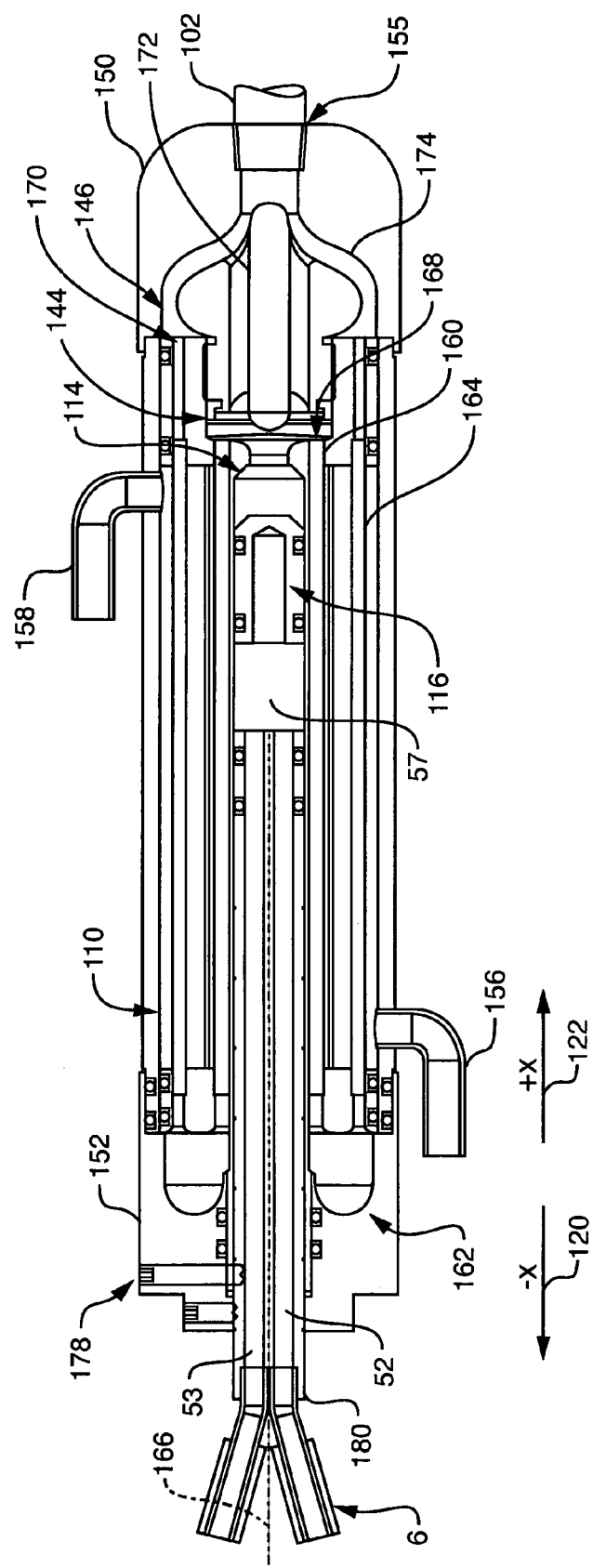
FIG. 6 illustrates a sectional view of the heat exchange assembly of FIG. 5, according to one embodiment of the invention.

The heat exchange conduit 110, as illustrated in FIG. 6, is configured as a substantially U-shaped conduit. The U-shaped conduit has a fluid inlet conduit 160, a bend conduit 164 in communication with the fluid inlet conduit 160, and an outlet conduit 164 in communication with the bend conduit 164. The fluid inlet conduit 160 and the fluid outlet conduit 164 orient substantially parallel to a central axis 166 defined by the heat exchange assembly 140. The U-shape of the bend conduit 164 provides a substantially laminar flow of blood from the fluid inlet conduit 160 to the fluid outlet conduit 164, thereby minimizing hemolysis of the red blood cell constituents of the blood.

The heat exchange conduit 110 of the heat exchange assembly 140 defines a heat exchange conduit volume where the heat exchange conduit volume is greater than the stroke volume defined by the pump 114. In such an arrangement, because the heat exchange conduit volume is greater than the stroke volume of the pump 114, the fluid that enters the heat exchange conduit 110 remains in thermal contact with the heat exchange fluid chamber 46 for a relatively long period of time or duration. Such time duration, therefore, allows efficient thermal adjustment (e.g., heating or cooling) of the fluid prior to the heat exchange assembly 2 reintroducing the fluid to the patient.

FIG. 6 illustrates the proximal covering 150 coupled to the heat exchange conduit covering 154. The proximal covering defines a fluid carrier port 155. In one arrangement, the fluid carrier port 155 is configured to receive and secure (e.g., via a friction fit) a catheter 1 to the heat exchange assembly 140.

Returning to FIG. 5, the check valve assembly 142 has a valve housing 141, a fluid inlet check valve 144, and a fluid outlet check valve 146. The check valve assembly 142 inserts within the proximal covering 150 of the heat exchange assembly 140. In one arrangement, the fluid inlet check valve 144 and fluid outlet check valve 146 are deformable and configured to direct fluid from a fluid carrier 102, such as a catheter, to the pump 114 or the heat exchange assembly 140, as described below. In one arrangement, the first check valve 144 and the second check valve 146 are formed as flexible membranes. For example, the first check valve 144 and the second check valve 146 are formed from a rubber material having a durometer value of between approximately 20 and 70 Shore.

Figure 7:
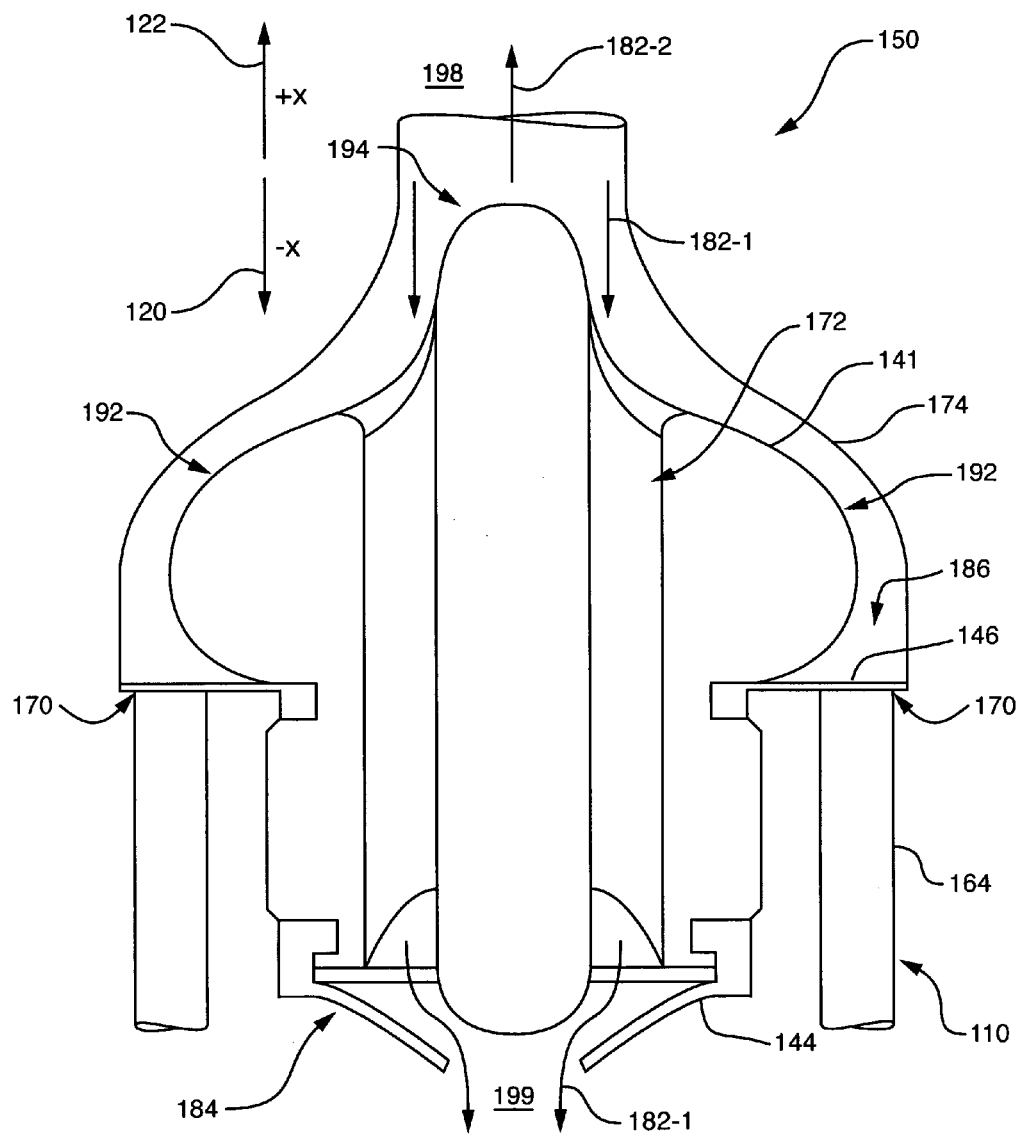
FIG. 7 illustrates a sectional view of a proximal end of the heat exchange assembly of FIG. 5, according to one embodiment of the invention.
Figure 8:
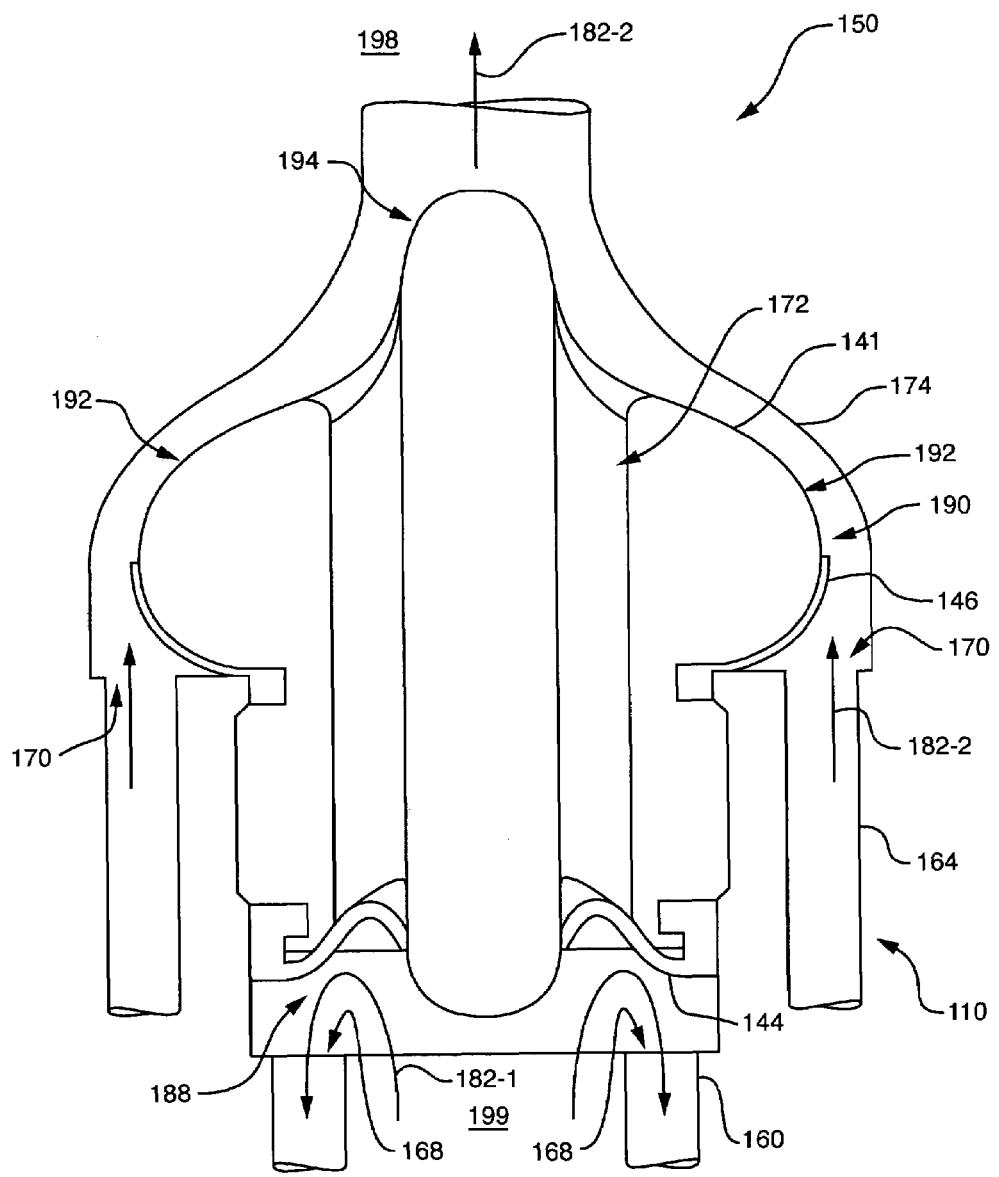
FIG. 8 illustrates a sectional view of a proximal end of the heat exchange assembly of FIG. 5, according to one embodiment of the invention.

In one arrangement, the valve housing 141 of the check valve assembly is hydrodynamically shaped. For example, as shown in FIG. 6, the check valve assembly 142 defines a fluid inlet path 172 in fluid communication between the fluid carrier port 155 (e.g., a first fluid region 198), as defined by the proximal covering 150, and the pump 114 (e.g., a second fluid region 199) of the heat exchange assembly 110. The entrance openings and exit openings defined by the fluid inlet path 172 form substantially curved shapes, as shown. Also as shown in FIG. 6, the valve housing 141 of the check valve assembly 142 defines a substantially curved fluid outlet path 174 in fluid communication between the fluid carrier port 155 and a fluid outlet 170 of the heat exchange conduit 110. For example, as illustrated in FIGS. 7 and 8, the valve housing 141 defines a first curve region 192 and a second curve region 194 that defines, relative to the central axis 166 defined by the heat exchange assembly 140, the substantially curved shape of the fluid outlet path 174.

The substantially curved configuration the fluid outlet path 174 allows the fluid outlet path 174 to bypass the fluid inlet path 172 such that both the fluid outlet path 174 and the fluid inlet path 172 fluidly communicate with the fluid carrier port 155. The substantially curved configuration of the entrance openings and exit openings defined by the fluid inlet path 172 and the fluid outlet path 174 (e.g., the hydrodynamic shape of the valve housing 141) provides a hydrodynamic flow effect (e.g., creates a hydrodynamic flow path) to blood entering or exiting the heat exchange assembly 140. For example, the hydrodynamic flow effect maintains laminar flow within the check valve assembly 142 when blood flows between the fluid carrier 102 (e.g., the first fluid region 198) and the pump 114 (e.g., the second fluid region 199) the heat exchange assembly 140. Such laminar flow minimizes exposure of the red blood cells of the blood to relatively high shear stresses, thereby minimizing induction of hemolysis in the red blood cells or destruction of particles in a fluid.

Returning to FIG. 6, as illustrated, the distal covering 152 couples to the heat exchange conduit covering 154. The distal covering 152 houses a pump suction tube 52 and pump pressure tube 53 that provide fluid communication between the pump 114 and the control console 66 via the umbilical 6. In one arrangement, the distal covering 152 also houses a stroke adjustment mechanism 178 configured to adjust a tube housing 180, relative to the pump 114, to adjust the volume of the actuation chamber 57 and, therefore, the stroke volume of the pump 114. For example, by moving the tube housing 180 along the −X direction 120, a user increases the stroke volume of the pump and by moving the tube housing 180 along the +X direction 122, the user decreases the stroke volume of the pump 114.

As indicated in FIG. 6, the fluid inlet check valve 144 orients in fluid communication with the fluid carrier 102 (e.g., in fluid communication with the fluid carrier port 155), in fluid communication with the pump 114, and in fluid communication with the fluid inlet 168 of the heat exchange conduit 110. Also as indicated in FIG. 6, the fluid outlet check valve 146 orients in fluid communication with the fluid carrier 102 (e.g., in fluid communication with the fluid carrier port 155) and in fluid communication with the fluid outlet 170 of the heat exchange conduit 110. During operation of the heat exchange assembly 140, the fluid inlet check valve 144 and a fluid outlet check valve 146 of the check valve assembly 142 actuate to direct fluid flow within the heat exchange assembly. The positioning of the check valves 144, 146 during actuation depends upon the stroke direction of the pump (e.g., fluid intake stroke versus fluid output stroke).

FIG. 7 illustrates positioning of the check valves 144, 146 during a fluid intake stroke of the pump 114. As the actuator 116 of the pump 114 actuates along the −X direction 120, the pump withdraws fluid 182-1, such as blood, from a patient, via fluid carrier 102, (e.g., from a first fluid region 198) such that the fluid 182-1 enters the fluid inlet path 172. During the fluid intake stroke of the pump 114, the fluid inlet check valve 144 engages a first position 184 that directs the fluid 182-1 from the fluid carrier 102, and from the fluid inlet path 172, to the pump 114. In one arrangement, the fluid inlet check valve 144 forms a hydrodynamic shape to create a hydrodynamic flow path for blood entering the pump 114, thereby maintaining laminar flow of the blood within the heat exchange assembly 140. Also during the fluid intake stroke of the pump 114, the pump 114 creates a pressure within the heat exchange assembly 140 that causes the fluid outlet check valve 146 to engage a first position 186. The first position 186 of the fluid outlet check valve 146 limits, or prevents, entry of the fluid 182-1 from the fluid carrier 102 to the fluid outlet 170 of the at least one heat exchange conduit 140.

FIG. 8 illustrates positioning of the check valves 144, 146 during a fluid output stroke of the pump 114. During the fluid output stroke of the pump 114 (e.g., as the actuator 116 of the pump 114 actuates along the +X direction 122), the fluid inlet check valve 144 engages a second position 188 that minimizes, or prevents, entry of the fluid 182-1 into the fluid inlet path 17 and directs the fluid 182-1 from the pump 114 to the fluid inlet 168 of the fluid inlet conduit 160 of the heat exchange conduit 110. As indicated above, the fluid inlet check valve 144 is formed of a flexible membrane. During a fluid output stroke of the pump 114, the fluid inlet check valve 144 defines a substantially curved flow path between the pump 114 and the fluid inlet 168 of the heat exchange conduit 110 (e.g., the fluid inlet check valve 144 conforms to the substantially curved shape of the exit opening defined by the fluid inlet path 172). In such an arrangement, the fluid inlet check valve 144 creates a hydrodynamic flow path for blood 182-1 reversing direction from the pump 114 to the heat exchange conduit 110. The hydrodynamic flow path maintains laminar flow of the blood within the heat exchange assembly 140 and minimizes hemolysis of the red blood cells of the blood (e.g., minimizing destruction of particles in the fluid).

Also during the fluid output stroke of the pump 114, the pump 114 drives existing (e.g., thermally altered) fluid 182-2 within the fluid outlet conduit 164 of the heat exchange conduit 110 into the fluid outlet path 174 of the heat exchange assembly 140. The fluid output stroke of the pump 114, therefore, causes the fluid outlet check valve 146 to engage a second position 190 that directs the fluid 182-2 from the fluid outlet 170 of the heat exchange conduit 110 to the fluid outlet path 174 and to the fluid carrier 102 (e.g., the second fluid region 198). As indicated above, the fluid inlet check valve 144 is formed of a flexible membrane. During a fluid output stroke of the pump 114, the fluid outlet check valve 146 defines a substantially curved flow path between the fluid outlet 170 of the heat exchange conduit 110 and the fluid carrier 102. In such an arrangement, the fluid outlet check valve 146 creates a hydrodynamic flow path (e.g., conforms to the substantially curved shape of the first curved region 192 of the valve housing 141) for blood 182-2 exiting the heat exchange conduit 110. The hydrodynamic flow path maintains laminar flow of the blood within the check valve assembly 141 (e.g., between the second fluid region 199 and the first fluid region 199) and minimizes hemolysis of the red blood cells of the blood.

Figure 9:
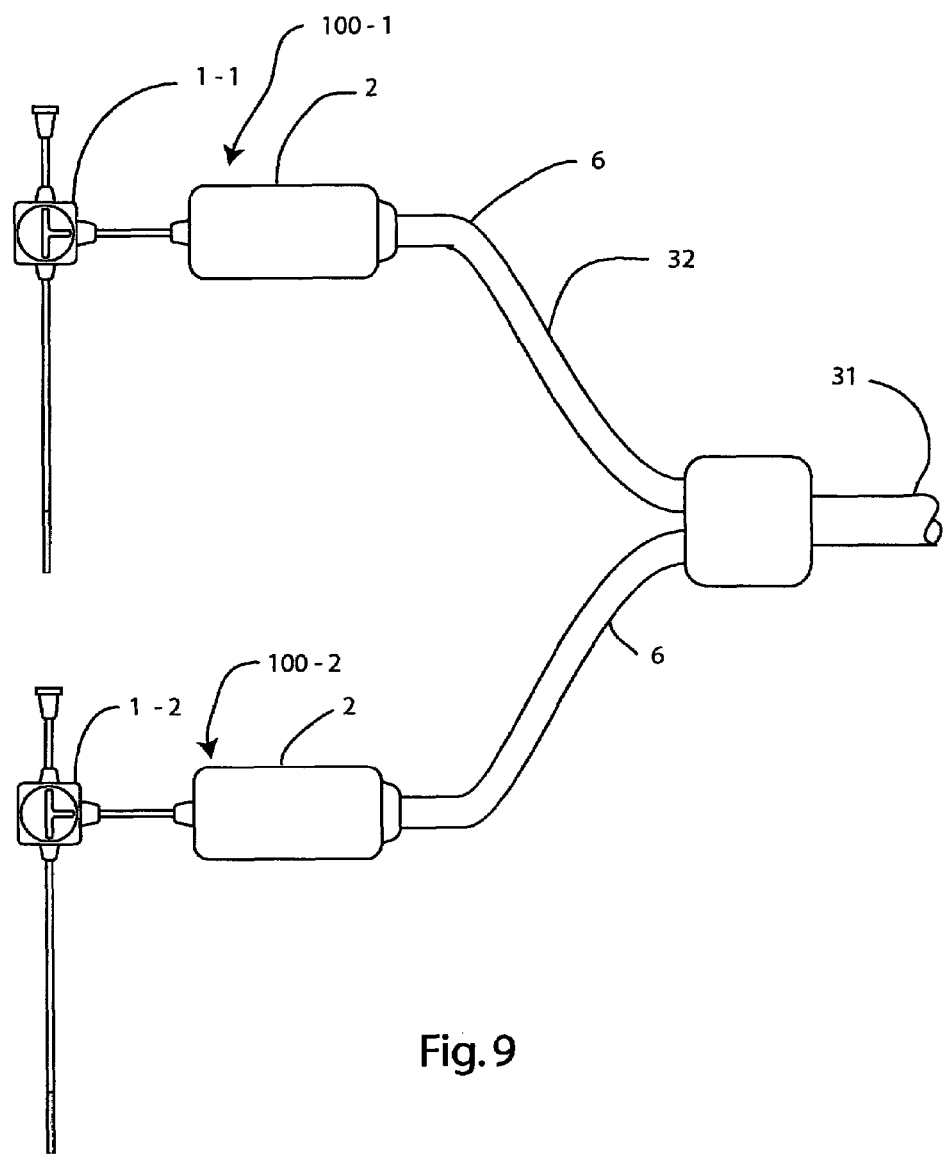
FIG. 9 depicts two vascular catheters configured with a common umbilical, according to one embodiment of the invention.

FIG. 9 depicts a bilateral carotid artery catheter assembly 32 having a first fluid transfer assembly 100-1, a second fluid transfer assembly 100-2 and a common umbilical 31. The bilateral carotid artery catheter assembly 32 is designed to provide selective head cooling where a first vascular catheter 1-1 is placed into a left common carotid artery and a second vascular catheter 1-2 is placed into a right common carotid artery. Both vascular catheters 1 are connected to a single control console 66 by the common umbilical 31 where the control console 66 allows operation of each vascular catheter 1 simultaneously and independently to thermally modify fluid entering a body lumen (e.g., cool blood entering a head).

Figure 10:
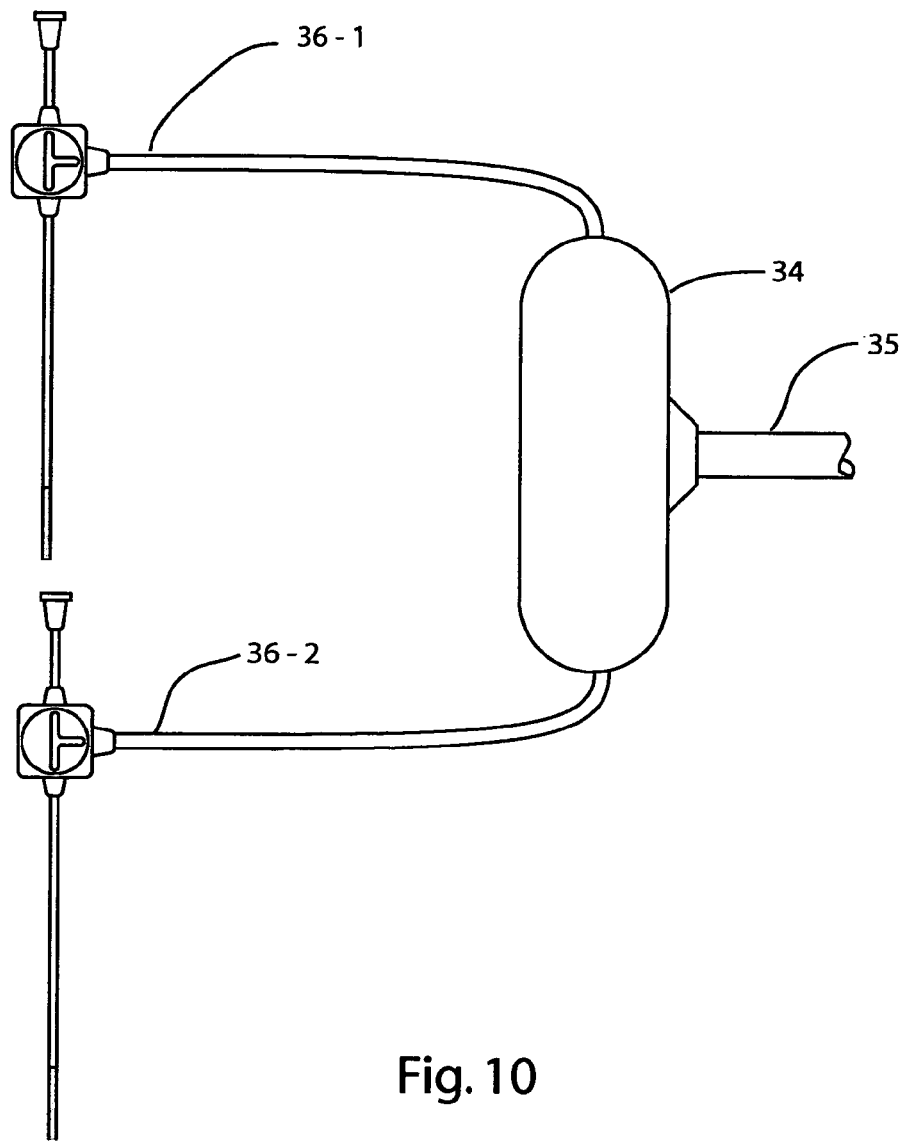
FIG. 10 depicts two vascular catheters configured with a common ex vivo heat exchange assembly, according to one embodiment of the invention.

FIG. 10 depicts a bilateral carotid artery catheter assembly 33 having a first vascular catheter 36-1 and a second vascular catheter 36-2. Instead of each catheter 36-1, 36-2 having a corresponding heat exchange assembly 2, the vascular catheters 36-1, 36-2 share a common heat exchange assembly 34 and a common umbilical 35. The common heat exchange assembly 34, in one arrangement, includes two heat exchangers and two pumps constructed such that a user can operate each vascular catheter 36-1, 36-2 simultaneously and independently. The bilateral carotid artery catheter assembly 33 is configured to provide selective head cooling where the first vascular catheter 36-1 is placed into a left common carotid artery, and the second vascular catheter 36-2 is placed into a right common carotid artery. Both vascular catheters 36-1, 36-2 are connected to a common heat exchange assembly 34 and a single control console 66 by a common umbilical 35. The control console allows operation of each vascular catheter 36-1, 36-2 simultaneously and independently.

Figure 11:
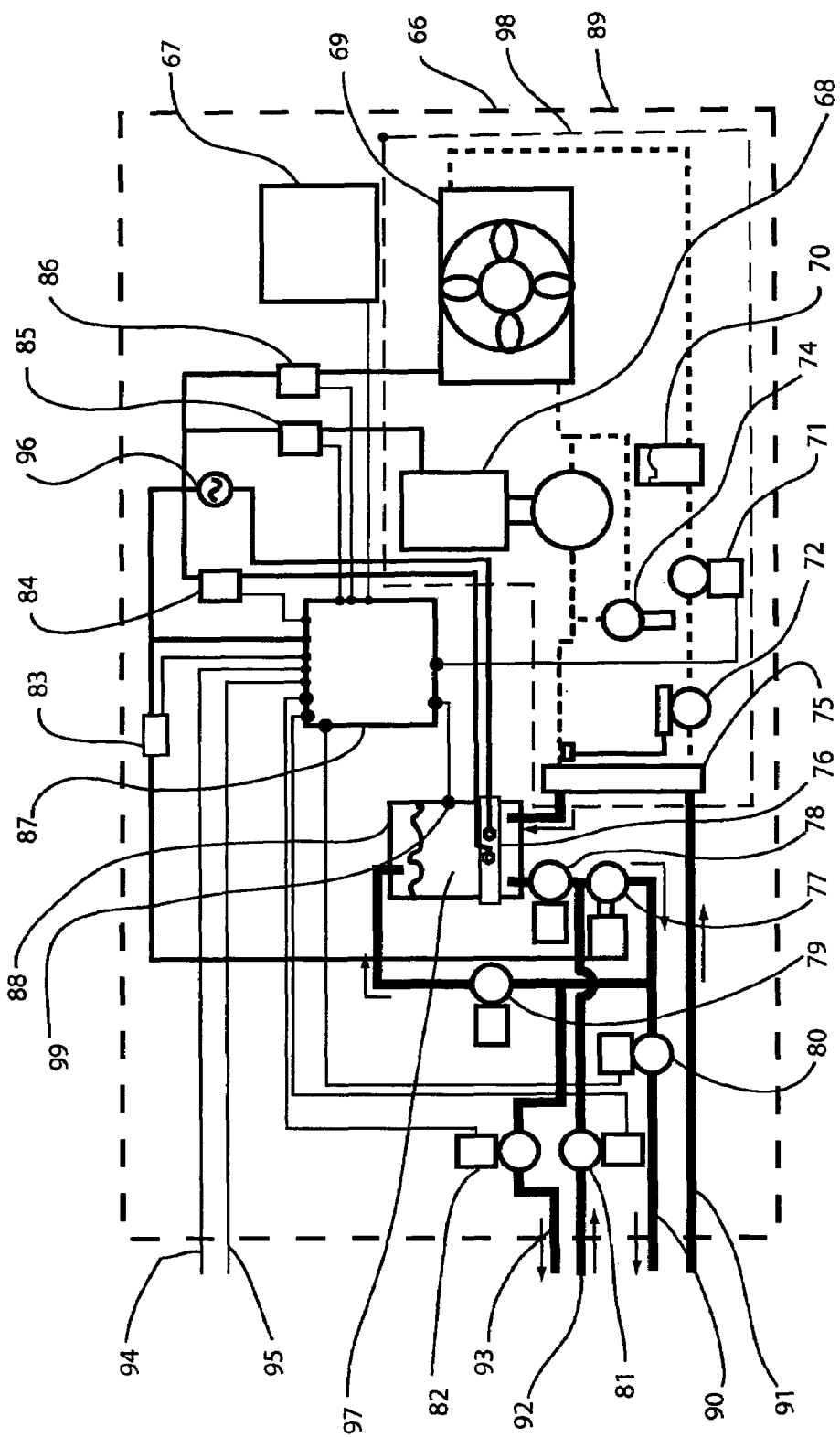
FIG. 11 depicts a schematic representation of a control console of the fluid transfer system, according to one embodiment of the invention.

FIG. 11 depicts, in schematic form, the control console 66, such as illustrated in FIG. 1, according to one embodiment of the invention. The control console 66 includes a console case 89, a refrigeration system 98, and an electrical control system. The refrigeration system 98 includes a compressor 68, a condenser 69, refrigerant accumulator 70, a solenoid valve 71, a hot gas bypass valve 74, a thermostatic expansion valve 72, and an evaporator/heat exchanger 75. The electrical control system has a user control and display panel 67, a mother board 87, relays 83, 84, 85, and 86, and an electrical power source 96.

The console 66 also has a secondary heat exchange circulation and blood pump actuation system that includes a reservoir 88, pressure regulator 78, pump 77, solenoid valve 80, solenoid valve 81, solenoid valve 82, pressure regulator 79, secondary heat exchange fluid return line 90, secondary heat exchange fluid outlet line 91, blood pump suction line 92, and blood pump pressure line 93, heater band. The console 66 also has a body temperature sensor lead, a heat exchange assembly sensor module lead 95, a connector configured to removably connect the catheter vascular catheter 1 to the control console 66, and a connector configured to removably connect at least one body temperature sensor to the control console 66.

The control and display panel 67 provides a user of the system 101 with controls necessary for operation of the system 101 and displays to provide the user information regarding the operation of the system 101. For example, the control panel 67 of the console 66 provides controls such as temperature control allowing the user to set the target temperature of the body of a patient, a rate control that allows the user to set a rate at which the patients body is cooled or warmed, a console power control, a primer assembly control to allow a user to prime the fluid carrier 102 and the heat exchange assembly 2 with blood prior to activating patient heating or cooling, and a deactivation control to allow a user to quickly stop the operation of the system 101. The display panel 67 of the console can include indications for current patient temperature, patient set point temperature, set cooling or heating rate, activation of safety interlocks, and the a current operating mode of the system 101.

The motherboard controls all functions of the system 101 according to control settings of the control panel 67, feedback from the sensor module 42, feedback from body temperature sensors coupled to the patient, and algorithms programmed into the control circuitry of the console 66. For example, if the temperature of the patient is to be lowered (e.g., such as indicated by feedback from the body temperature sensors), heat exchange fluid 97 in the reservoir 88 is cooled by the refrigeration system 98 as the heat exchange fluid 97 passes through the evaporator/heat exchanger 75. If the temperature of the patient is to be increased (e.g., such as indicated by feedback from the body temperature sensors), heat exchange fluid 97 in the reservoir 88 is heated by the electric heating band 76. The reservoir temperature sensor 99 provides signals to the control system that indicate the temperature of secondary heat exchange fluid 97 in the reservoir 88. Such signals, in turn, activate the refrigeration system 98 or heating band 76 according to the desired result (e.g., patient cooling or patient heating).

The pump 77 of the console 66 pumps heat exchange fluid 97 from the reservoir 88, through the heat exchange assembly 2, as described above, and back to the reservoir 88 to cool or heat the patient's blood. Actuation of the solenoid valve 80 (e.g., actuated in an open or closed manner) controls the flow (e.g. flow rate) of heat exchange fluid 97 from the console 66 and into the heat exchange assembly 2, according to signals received from the sensor module 42, to control the temperature of the blood retuned to the patient from heat exchange assembly 2.

The pressure regulator 78 provides a predetermined negative gage pressure on a suction side of the pump 77 and a pressure regulator 79 provides a predetermined positive gage pressure on a high-pressure side of pump 77. Such pressure actuates an actuator 116 of the pump 114. The solenoid valve 81 and the solenoid valve 82 controls blood pump actuation in the heat exchange assembly 2. During normal operation, the solenoid valve 81 is opened and solenoid valve 82 is closed to draw blood into the chamber 58. The solenoid valve 81 is closed and the solenoid valve 82 is opened to push blood out of the chamber 58. By opening the solenoid valve 81 and closing the solenoid valve 82, the console 66 applies suction to the actuation chamber 57. By closing the solenoid valve 81 and opening the solenoid valve 82, the console 66 applies pressure to the actuation chamber 57.

To remove the air from the blood pump actuation chamber 57, the pump suction tube 52 and the pump pressure tube 53 of the heat exchange assembly 2, the pump suction line 92, the pump pressure line 93, and both solenoid valves 81, 82 are placed into a open position to allow heat exchange fluid to flow through the lines and displace any air within the lines.

When the sensor module 42 detects the presence of emboli, the circuitry of motherboard 87 places both solenoid valves 81 and 82 into a closed position. The relay 83 turns the pump 77 "on" or "off" according to signals received from motherboard 87. The relay 84 turns the heating band 76 "on" or "off" according to signals received from the motherboard 87. The relay 85 turns the refrigeration compressor 68 "on" or "off" according to signals received from motherboard 87. The relay 86 turns the condenser 76 "on" or "off" according to signals received from motherboard 87. The solenoid valve 71 controls the flow of refrigerant into evaporator/heat exchanger 75 to cool the heat exchange fluid 97 in reservoir 88 according to signals received by motherboard 87 from temperature sensor 99. The operation of the compressor, condenser 69, refrigerant accumulator 70, hot gas bypass valve 74, and thermostatic expansion valve 72 is known in the refrigeration art. The evaporator/heat exchanger 75, in one arrangement, is formed of counter flow concentric tube design.

The electric power source of the console can be external AC wall power, internal batteries, or an internal generator powered by an internal combustion engine. In the case where the console receives power via internal batteries, the console 66 can be transported and operated in a pre-hospital setting, such as by military medics treating injured soldiers on a battlefield. The maximum heat load required to manage the temperature of a patient is approximately 400 to 500 watts including ambient heat loss or gain, therefore, the refrigeration system 98, and the heater band 76 can be sized appropriately. The pump 80 can be positive displacement pump to avoid added heat due to pump friction having a capacity for pumping fluid at approximately 30 to 100 PSI at a rate of approximately 1 to 3 gallons per minute.

Figure 12:
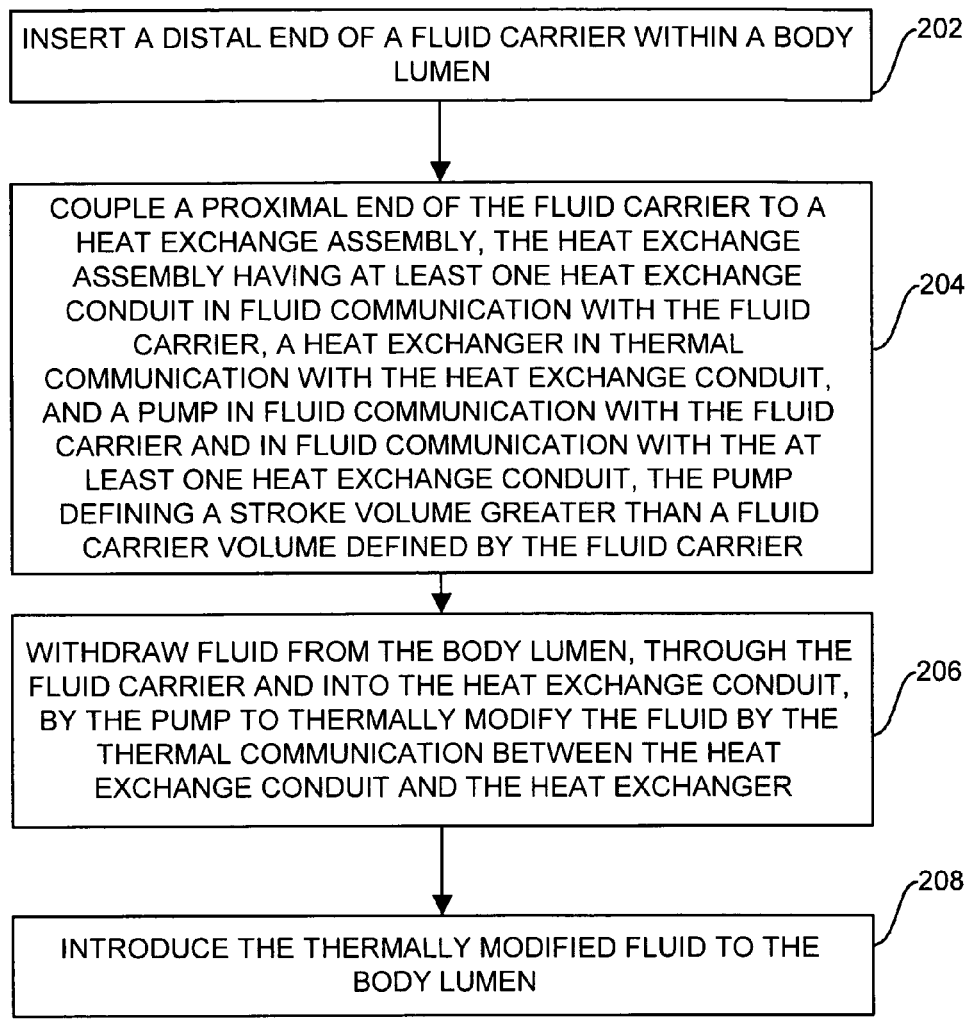
FIG. 12 illustrates a flowchart of a procedure for obtaining a therapeutic temperature in a body, according to one embodiment of the invention.

FIG. 12 illustrates a flowchart 200 of a procedure for obtaining a therapeutic temperature in a body. The procedure can be performed by a health care professional, such as a surgeon.

In step 202, a user inserts a distal end of a fluid carrier 102 within a body lumen. For example, in one arrangement, inserting a distal end 10 of a catheter 1 within a carotid artery of a body.

In step 204, the user couples a proximal end of the fluid carrier 102 to a heat exchange assembly 2, the heat exchange assembly 2 having a heat exchange conduit 110 in fluid communication with the fluid carrier 102, a heat exchanger 112 in thermal communication with the heat exchange conduit 110, and a pump 114 in fluid communication with the fluid carrier 102 and in fluid communication with the heat exchange conduit. The pump 114 defines a stroke volume greater than a fluid carrier volume defined by the fluid carrier 102.

In step 206, the user withdraws fluid from the body lumen, through the fluid carrier 102 and into the heat exchange conduit 110, using the pump, to thermally modify the fluid by the thermal communication between the heat exchange conduit 110 and the heat exchanger 112. In one arrangement, the user activates a pump associated with the console 66 to activate the pump 114 to withdraw fluid from the body lumen.

In step 208, the user introduces the thermally modified fluid to the body lumen. The user can then repeats steps 206, 207, and 208 until the user detects a body temperature of the body as being substantially equal to a preset therapeutic temperature.

While this invention has been particularly shown and described with references to preferred embodiments thereof, it will be understood by those skilled in the art that various changes in form and details may be made therein without departing from the spirit and scope of the invention as defined by the appended claims.

As described above, the catheter 1 can be configured to insert within a carotid artery of a patient (e.g., the catheter 1 is configured as a carotid artery catheter). Such description is by way of example only. In another arrangement, the catheter 1 is configured as a central venous catheter. The central venous catheter allows a user to infuse fluids into a patient, extract blood from the patient, and, in conjunction with an ex vivo heat exchanger, control the temperature of the body of the patient where the patient is suffering from hypovolemia, cardiac arrest, myocardial infarction, stroke, subarachnoid hemorrhage, brain trauma, or brain hemorrhage.

FIG. 1 illustrates the catheter 1 (e.g., a long axis of the catheter 1) oriented at an angle approximately 90° relative to a long axis of the heat exchange assembly 2. Such illustration is by way of example only. In another arrangement, a long axis of the catheter 1 orients substantially parallel to a long axis of the heat exchange assembly 2. When the catheter inserts within a blood vessel of a patient, such orientation, maintains laminar flow of blood within the catheter 1 during a fluid intake stroke and a fluid output stroke of the pump 114 to minimize exposure of red blood cells of the blood to relatively high shear stresses, thereby minimizing induction of hemolysis in the red blood cells.

As described above, the fluid transfer system 101 operates to remove fluid, such as blood, from a patient, thermally alter (e.g., heat or cool) the fluid, and return the fluid to the patient. The fluid transfer system 101, in one arrangement, is configured to operate with other equipment used in treating a patient in the emergent care setting. For example, the fluid transfer system 101 operates with electrocardiogram (EKG) sensors or pulse oximetry sensors, blood chemical sensors, such as blood gas sensors, and defibrillators. The fluid transfer system also operates with infusion pumps to infuse blood, blood plasma, saline, Ringer's lactate, or medications into the patient.

What is claimed is:

1. A fluid transfer assembly comprising:
   a fluid carrier defining a fluid carrier volume, the fluid carrier having a distal end and a proximal end, the distal end configured to insert within a body lumen; and
   a heat exchange assembly coupled to the proximal end of the fluid carrier, the heat exchange assembly having:
   at least one heat exchange conduit in fluid communication with the fluid carrier;
   a heat exchanger in thermal communication with the heat exchange conduit; and
   a pump in fluid communication with the fluid carrier and in fluid communication with the at least one heat exchange conduit, the pump defining a stroke volume greater than the fluid carrier volume defined by the fluid carrier, the at least one heat exchange conduit defining a heat exchange conduit volume greater than the stroke volume defined by the pump.

2. The fluid transfer assembly of claim 1 wherein the fluid carrier volume of the fluid carrier is less than between 30% and 60% of the stroke volume defined by the pump.

3. The fluid transfer assembly of claim 1 wherein the heat exchange assembly comprises a fluid inlet check valve in fluid communication with the fluid carrier, in fluid communication with the pump, and in fluid communication with a fluid inlet of the at least one heat exchange conduit, the fluid inlet check valve configured to:
   (i) engage a first position during a fluid intake stroke of the pump, the first position of the fluid inlet check valve directing a fluid from the fluid carrier to the pump; and (ii) engage a second position during a fluid output stroke of the pump, the second position of the fluid inlet check valve directing the fluid from the pump to the fluid inlet of the at least one heat exchange conduit.

4. The fluid transfer assembly of claim 3 wherein the fluid inlet check valve comprises a flexible membrane that defines a substantially curved flow path between the pump and the fluid inlet of the at least one heat exchange conduit when the fluid inlet check valve engages the second position during the fluid output stroke of the pump.

5. The fluid transfer assembly of claim 1 wherein the heat exchange assembly comprises a fluid outlet check valve in fluid communication with the fluid carrier and in fluid communication with a fluid outlet of the at least one heat exchange conduit, the fluid outlet check valve configured to:
  (i) engage a first position during a fluid intake stroke of the pump, the first position of the fluid outlet check valve limiting entry of a fluid from the fluid carrier to the fluid outlet of the at least one heat exchange conduit; and
  (ii) engage a second position during a fluid output stroke of the pump, the second position of the fluid outlet check valve directing the fluid from the fluid outlet of the at least one heat exchange conduit to the fluid carrier.

6. The fluid transfer assembly of claim 5 wherein the fluid outlet check valve comprises a flexible membrane that defines a substantially curved flow path between the fluid outlet of the at least one heat exchange conduit and the fluid carrier when the fluid outlet check valve engages the second position during the fluid output stroke of the pump.

7. The fluid transfer assembly of claim 1 wherein the heat exchange assembly defines a substantially curved fluid outlet path, relative to a central axis defined by the heat exchange assembly, disposed between the fluid carrier and a fluid outlet of the at least one heat exchange conduit.

8. The fluid transfer assembly of claim 1 wherein the heat exchange conduit is configured as a coiled-shaped conduit relative to a central axis defined by the heat exchange assembly.

9. The fluid transfer assembly of claim 1 wherein the heat exchange conduit is configured as a substantially U-shaped conduit having a fluid inlet conduit, a bend conduit in communication with the fluid inlet conduit, and an outlet conduit in communication with the bend conduit, the fluid inlet conduit and the fluid outlet conduit substantially parallel to a central axis defined by the heat exchange assembly.

10. The fluid transfer assembly of claim 1 wherein the heat exchange assembly comprises a first check valve in fluid communication with the fluid carrier, in fluid communication with the pump, and in fluid communication with a fluid inlet of the at least one heat exchange conduit, the first check valve configured to:
  (i) engage a first position during a fluid intake stroke of the pump, the first position of the first check valve directing a fluid from the fluid carrier to the fluid inlet of the at least one heat exchange conduit; and
  (ii) engage a second position during a fluid output stroke of the pump, the second position of the first check valve directing the fluid from the pump to the fluid carrier.

11. The fluid transfer assembly of claim 1 wherein the heat exchange assembly comprises a second check valve in fluid communication with the pump and in fluid communication with a fluid outlet of the at least one heat exchange conduit, the second check valve configured to:
  (i) engage a first position during a fluid intake stroke of the pump, the first position of the second check valve directing a fluid from the fluid outlet of the at least one heat exchange conduit to the pump; and
  (ii) engage a second position during a fluid output stroke of the pump, the second position of the second check valve limiting entry of the fluid from the pump to the fluid outlet of the at least one heat exchange conduit.

12. The fluid transfer assembly of claim 1 wherein the heat exchange assembly comprises a sensor in fluid communication with the fluid carrier, the sensor chosen from the group consisting of a temperature sensor, a blood flow rate sensor, a bubble sensor, or a clot detection sensor.

13. The fluid transfer assembly of claim 1 wherein the fluid carrier comprises a catheter defining a lumen, the catheter configured to:
  (i) provide fluid, via the lumen, from the body lumen and to the heat exchange assembly during a fluid intake stroke of the pump; and
  (ii) deliver fluid, via the lumen, from the heat exchange assembly and to the body lumen during a fluid output stroke of the pump.

14. The fluid transfer assembly of claim 1 wherein the fluid carrier comprises a catheter configured to insert within a carotid artery of a body.

15. The fluid transfer assembly of claim 14 wherein the catheter has a diameter between 4 French and 18 French.

16. The fluid transfer assembly of claim 1 wherein the fluid carrier comprises a double-lumen catheter defining a first lumen and a second lumen, the catheter configured to:
  (i) provide fluid, via the first lumen, from the body lumen and to the heat exchange assembly during a fluid intake stroke of the pump; and
  (ii) deliver fluid, via the second lumen, from the heat exchange assembly and to a body lumen during a fluid output stroke of the pump.

17. The fluid transfer assembly of claim 1 wherein the fluid carrier comprises priming assembly configured to introduce fluid into, and remove air from, the heat exchange conduit.

18. The fluid transfer assembly of claim 1 wherein the fluid carrier comprises a catheter configured to insert within a lateral ventricle of a brain.

19. A fluid transfer system comprising:
  a fluid carrier defining a fluid carrier volume, the fluid carrier having a distal end and a proximal end, the distal end configured to insert within a body lumen;
  a heat exchange assembly coupled to the proximal end of the fluid carrier, the heat exchange assembly having:
    at least one heat exchange conduit in fluid communication with the fluid carrier,
    a heat exchanger in thermal communication with the heat exchange conduit, and
    a pump in fluid communication with the fluid carrier and in fluid communication with the at least one heat exchange conduit, the pump defining a stroke volume greater than the fluid carrier volume defined by the fluid carrier, the at least one heat exchange conduit defining a heat exchange conduit volume greater than the stroke volume defined by the pump; and
  a console coupled to the heat exchange assembly, the console configured to circulate a thermal exchange fluid within the heat exchanger of the heat exchange assembly.

20. The fluid transfer system of claim 19 wherein the fluid carrier volume of the fluid carrier is less than between 30% and 60% of the stroke volume defined by the pump.

21. The fluid transfer system of claim 19 wherein the heat exchange assembly comprises a fluid inlet check valve in fluid communication with the fluid carrier, in fluid communication with the pump, and in fluid Communication with a fluid inlet of the at least one heat exchange conduit, the fluid inlet check valve configured to:
(i) engage a first position during a fluid intake stroke of the pump, the first position of the fluid inlet check valve directing a fluid from the fluid carrier to the pump; and
(ii) engage a second position during a fluid output stroke of the pump, the second position of the fluid inlet check valve directing the fluid from the pump to the fluid inlet of the at least one heat exchange conduit.

22. The fluid transfer system of claim 21 wherein the fluid inlet check valve comprises a flexible membrane that defines a substantially curved flow path between the pump and the fluid inlet of the at least one heat exchange conduit when the fluid inlet check valve engages the second position during the fluid output stroke of the pump.

23. The fluid transfer system of claim 19 wherein the heat exchange assembly comprises a fluid outlet check valve in fluid communication with the fluid carrier and in fluid communication with a fluid outlet of the at least one heat exchange conduit, the fluid outlet check valve configured to:
(i) engage a first position during a fluid intake stroke of the pump, the first position of the fluid outlet check valve limiting entry of the fluid from the fluid carrier to the fluid outlet of the at least one heat exchange conduit; and
(ii) engage a second position during a fluid output stroke of the pump, the second position of the fluid outlet check valve directing the fluid from the fluid outlet of the at least one heat exchange conduit to the fluid carrier.

24. The fluid transfer system of claim 23 wherein the fluid outlet check valve comprises a flexible membrane that defines a substantially curved flow path between the fluid outlet of the at least one heat exchange conduit and the fluid carrier when the fluid outlet check valve engages the second position during the fluid output stroke of the pump.

25. The fluid transfer system of claim 19 wherein the heat exchange assembly defines a substantially curved fluid outlet path, relative to a central axis defined by the heat exchange assembly, disposed between the fluid carrier and a fluid outlet of the at least one heat exchange conduit.

26. The fluid transfer system of claim 19 wherein the heat exchange conduit is configured as a coiled-shaped conduit relative to a central axis defined by the heat exchange assembly.

27. The fluid transfer system of claim 19 wherein the heat exchange conduit is configured as a substantially U-shaped conduit having a fluid inlet conduit, a bend conduit in communication with the fluid inlet conduit, and an outlet conduit in communication with the bend conduit, the fluid inlet conduit and the fluid outlet conduit substantially parallel to a central axis defined by the heat exchange assembly.

28. The fluid transfer system of claim 19 wherein the heat exchange assembly comprises a first check valve in fluid communication with the fluid carrier, in fluid communication with the pump, and in fluid communication with a fluid inlet of the at least one heat exchange conduit, the first check valve configured to:
(i) engage a first position during a fluid intake stroke of the pump, the first position of the first check valve directing a fluid from the fluid carrier to the fluid inlet of the at least one heat exchange conduit; and
(ii) engage a second position during a fluid output stroke of the pump, the second position of the first check valve directing the fluid from the pump to the fluid carrier.

29. The fluid transfer system of claim 19 wherein the heat exchange assembly comprises a second check valve in fluid communication with the pump and in fluid communication with a fluid outlet of the at least one heat exchange conduit, the second check valve configured to:
(i) engage a first position during a fluid intake stroke of the pump, the first position of the second check valve directing the fluid from the fluid outlet of the at least one heat exchange conduit to the pump; and
(ii) engage a second position during a fluid output stroke of the pump, the second position of the second check valve limiting entry of the fluid from the pump to the fluid outlet of the at least one heat exchange conduit.

30. The fluid transfer system of claim 19 wherein the heat exchange assembly comprises a sensor in fluid communication with the fluid carrier and in electrical communication with the console, the sensor chosen from the group consisting of a temperature sensor, a blood flow rate sensor, a bubble sensor, or a clot detection sensor.

31. The fluid transfer system of claim 19 wherein the fluid carrier comprises a catheter defining a lumen, the catheter configured to:
(i) provide fluid, via the lumen, from the body lumen and to the heat exchange assembly during a fluid intake stroke of the pump; and
(ii) deliver fluid, via the lumen, from the heat exchange assembly and to the body lumen during a fluid output stroke of the pump.

32. The fluid transfer system of claim 19 wherein the fluid carrier comprises a catheter configured to insert within a carotid artery of a body.

33. The fluid transfer system of claim 32 wherein the catheter has a diameter between 4 French and 18 French.

34. The fluid transfer system of claim 19 wherein the fluid carrier comprises a double-lumen catheter defining a first lumen and a second lumen, the catheter configured to:
(i) provide fluid, via the first lumen, from the body lumen and to the heat exchange assembly during a fluid intake stroke of the pump; and
(ii) deliver fluid, via the second lumen, from the heat exchange assembly and to a body lumen during a fluid output stroke of the pump.

35. The fluid transfer assembly of claim 19 wherein the fluid carrier comprises priming assembly configured to introduce fluid into, and remove air from, the heat exchange conduit.

36. The fluid transfer system of claim 19 wherein the fluid carrier comprises a catheter configured to insert within a lateral ventricle of a brain.

37. A heat exchange assembly configured to couple in fluid communication with a fluid carrier, a distal end of the fluid carrier configured to insert within a body lumen, the heat exchange assembly comprising:
at least one heat exchange conduit defusing a heat exchange conduit volume;
a heat exchanger in thermal communication with the heat exchange conduit; and
a pump in fluid communication with the at least one heat exchange conduit, the pump defining a stroke volume, the heat exchange conduit volume defined by the at least one heat exchange conduit being greater than the stroke volume defined by the pump.

38. The heat exchange assembly of claim 37 comprising a fluid inlet check valve configured to couple in fluid communication with the fluid carrier, in fluid communication with the pump, and in fluid communication with a fluid inlet of the at least one heat exchange conduit, the fluid inlet check valve configured to:
- (i) engage a first position during a fluid intake stroke of the pump, the first position of the fluid inlet check valve configured to direct a fluid from the fluid carrier to the pump; and
- (ii) engage a second position during a fluid output stroke of the pump, the second position of the fluid inlet check valve directing the fluid from the pump to the fluid inlet of the at least one heat exchange conduit.

39. The heat exchange assembly of claim 38 wherein the fluid inlet check valve comprises a flexible membrane that defines a substantially curved flow path between the pump and the fluid inlet of the at least one heat exchange conduit when the fluid inlet check valve engages the second position during the fluid output stroke of the pump.

40. The heat exchange assembly of claim 37 wherein the heat exchange assembly comprises a fluid outlet check valve configured to couple in fluid communication with the fluid carrier and in fluid communication with a fluid outlet of the at least one heat exchange conduit, the fluid outlet check valve configured to:
- (i) engage a first position during a fluid intake stroke of the pump, the first position of the fluid outlet check valve configured to limit entry of a fluid from the fluid carrier to the fluid outlet of the at least one heat exchange conduit; and
- (ii) engage a second position during a fluid output stroke of the pump, the second position of the fluid outlet check valve directing the fluid, from the fluid outlet of the at least one heat exchange conduit to the fluid carrier.

41. The heat exchange assembly of claim 40 wherein the fluid outlet check valve comprises a flexible membrane that defines a substantially curved flow path between the fluid outlet of the at least one heat exchange conduit and the fluid carrier when the fluid outlet check valve engages the second position during the fluid output stroke of the pump.

42. The heat exchange assembly of claim 37 wherein the heat exchange assembly defines a substantially curved fluid outlet path, relative to a central axis defined by the heat exchange assembly, disposed between the fluid carrier and a fluid outlet of the at least one heat exchange conduit.

43. The heat exchange assembly of claim 37 wherein the heat exchange conduit is configured as a coiled-shaped conduit relative to a central axis defined by the heat exchange assembly.

44. The heat exchange assembly of claim 37 wherein the heat exchange conduit is configured as a substantially U-shaped conduit having a fluid inlet conduit, a bend conduit in communication with the fluid inlet conduit, and an outlet conduit in communication with the bend conduit, the fluid inlet conduit and the fluid outlet conduit substantially parallel to a central axis defined by the heat exchange assembly.

45. The heat exchange assembly of claim 37 comprising a sensor in fluid communication with the fluid carrier, the sensor chosen from the group consisting of a temperature sensor, a blood flow rate sensor, a bubble sensor, or a clot detection sensor.

46. A method for obtaining a therapeutic temperature in a body comprising:
- inserting a distal end of a fluid carrier within a body lumen;
- coupling a proximal end of the fluid carrier to a heat exchange assembly, the heat exchange assembly having at least one heat exchange conduit in fluid communication with the fluid carrier, a heat exchanger in thermal communication with the heat exchange conduit, and a pump in fluid communication with the fluid carrier and in fluid communication with the at least one heat exchange conduit, the pump defining a stroke volume greater than a fluid carrier volume defined by the fluid carrier;
- detecting the temperature of the body;
- withdrawing fluid from the body lumen, through the fluid carrier and into the heat exchange conduit, by the pump to thermally modify the fluid by the thermal communication between the heat exchange conduit and the heat exchanger;
- introducing the thermally modified fluid to the body lumen; and
- repeating the steps of withdrawing and introducing until a detected body temperature is substantially equal to a preset therapeutic temperature.

47. The method of claim 46 wherein the step of inserting comprises inserting a distal end of a catheter within a carotid artery of a body and further comprising selectively cooling a head of the body by:
- withdrawing blood from the carotid artery body lumen, through the catheter and into the heat exchange conduit, by the pump;
- cooling the blood by the thermal communication between the heat exchange conduit and the heat exchanger; and
- introducing the cooled blood to the body lumen.

* * * * *

UNITED STATES PATENT AND TRADEMARK OFFICE
CERTIFICATE OF CORRECTION

| | | |
|---|---|---|
| PATENT NO. | : 7,241,307 B2 | Page 1 of 1 |
| APPLICATION NO. | : 10/758687 | |
| DATED | : July 10, 2007 | |
| INVENTOR(S) | : Charles D. Lennox | |

It is certified that error appears in the above-identified patent and that said Letters Patent is hereby corrected as shown below:

In the Claims:

Column 27, line 2, in claim 21, change "Communication" to --communication--.

Signed and Sealed this

Second Day of October, 2007

JON W. DUDAS
*Director of the United States Patent and Trademark Office*